United States Patent
Le et al.

(10) Patent No.: US 6,488,880 B2
(45) Date of Patent: Dec. 3, 2002

(54) METHOD OF MAKING A GRADIENT GEL WITH A MOVABLE DISPENSING TIP

(75) Inventors: Ngoc-Anh Le, Decatur, GA (US); Xianzhou Li, Decatur, GA (US); Wendy Innis-Whitehouse, Snellville, GA (US); Keith Gray, Norcross, GA (US)

(73) Assignee: Clinical Laboratory Development Group, Inc., Atlanta, GA (US)

( * ) Notice: Subject to any disclaimer, the term of this patent is extended or adjusted under 35 U.S.C. 154(b) by 0 days.

(21) Appl. No.: 09/848,484

(22) Filed: May 3, 2001

(65) Prior Publication Data

US 2001/0018064 A1 Aug. 30, 2001

Related U.S. Application Data

(62) Division of application No. 09/219,402, filed on Dec. 23, 1998, now Pat. No. 6,267,579.

(51) Int. Cl.[7] .................. B29C 35/02; B29C 35/08; B29C 39/02
(52) U.S. Cl. ............. 264/267; 264/299; 264/496; 204/619; 204/620
(58) Field of Search ............... 264/240, 267, 264/299, 260, 259, 494, 496; 425/110, 256, 258; 204/606, 619, 620

(56) References Cited

U.S. PATENT DOCUMENTS

| | | | |
|---|---|---|---|
| 3,719,580 A | * 3/1973 | Roberts et al. | 204/619 |
| 4,088,561 A | * 5/1978 | Anderson | 204/610 |
| 4,111,785 A | * 9/1978 | Roskam | 204/615 |
| 4,169,036 A | 9/1979 | Anderson et al. | 204/299 R |
| 4,479,861 A | * 10/1984 | Hediger | 204/615 |
| 4,533,307 A | 8/1985 | Ansorge | 425/90 |
| 4,594,064 A | 6/1986 | Anderson | 425/145 |
| 5,082,548 A | * 1/1992 | Faupel et al. | 204/644 |
| 5,540,498 A | 7/1996 | Chu | 366/160.4 |
| 5,589,104 A | 12/1996 | Bambeck | 252/315 |
| 5,876,741 A | * 3/1999 | Ron | 424/423 |
| 5,888,369 A | * 3/1999 | Tippins et al. | 204/456 |
| 5,925,229 A | 7/1999 | Krauss et al. | 204/606 |
| 5,993,627 A | * 11/1999 | Anderson et al. | 204/456 |
| 6,187,250 B1 | * 2/2001 | Champagne | 204/470 |

OTHER PUBLICATIONS

Singh et al., "Effects of diabetes on lipoprotein size," Arterioscl. Thromb. Vasc. Biol. 15: 1805–1811 (1995).

Rainwater et al., "Production of polyacrylamide gradient gels for the electrophoretic resolution of lipoproteins," J. Lipid. Res. 33: 1876–1881 (1992).

(List continued on next page.)

*Primary Examiner*—Angela Ortiz
(74) *Attorney, Agent, or Firm*—Merchant & Gould; Tim Tingkang Xia

(57) ABSTRACT

An apparatus and method for making a gradient gel. The present invention in one embodiment is a gel-making system that has a reservoir for holding a solution. The reservoir is connected to a movable arm through a tubing. The tubing has two ends: one end is in fluid communication with the reservoir; and the other, an open end, is received by the movable arm. A gel holder having an internal gel chamber is placed underneath the movable arm for receiving the solution. In operation, the movement of the movable arm causes the open end of the tubing to move along with it and the open end of the tubing delivers the solution in motion to the internal gel chamber to form the gel.

12 Claims, 10 Drawing Sheets

OTHER PUBLICATIONS

Cheung et al., "Altered particle size distribution of apoA-containing lipoproteins in subjects with coronary artery disease," J. Lipid Res. 32:383–397 (1991).

Johansson et al, "High Density Lipoproteins and Coronary Atherosclerosis," Arterioscl. Thromb. 11: 174–182 (1991).

Gambert et al., "Human low density lipoprotein fractions separated by gradient gel electrophoresis: Composition, distribution and alterations induced by cholesteryl ester transfer protein," J. Lipid Res. 31: 1199–1210 (1990).

Austin et al., "Low–density lipoprotein subclass patterns and risk of myocardial infarction," J. Amer. Med. Assoc. 260: 1917–1921(4) (1988).

Austin et al., "Inheritance of Low–density lipoprotein subclass patterns: results of complex segregation analysis," Am J Hum Genet 43:838–876 (5) (1988).

Austin et al., "Genetic control of low density lipoprotein subclasses," Lancet 2: 592–595(3) (1986).

Blanche et al., "Characterization of human high density lipoproteins by gradient gel electrophoresis," Biochim Biophys Acta 665: 408–419 (1981).

Slyper, "Low–Density Lipoprotein Density and Atherosclerosis," JAMA, vol. 272, No. 4 (Jul. 27, 1994).

Superko, "Small Dense LDL: The Coronary Artery Disease Risk Factor and How it is Changing the Treatment of CAD," Preventive Cardiology, Winter 1998, pp. 16–24 (1997).

* cited by examiner

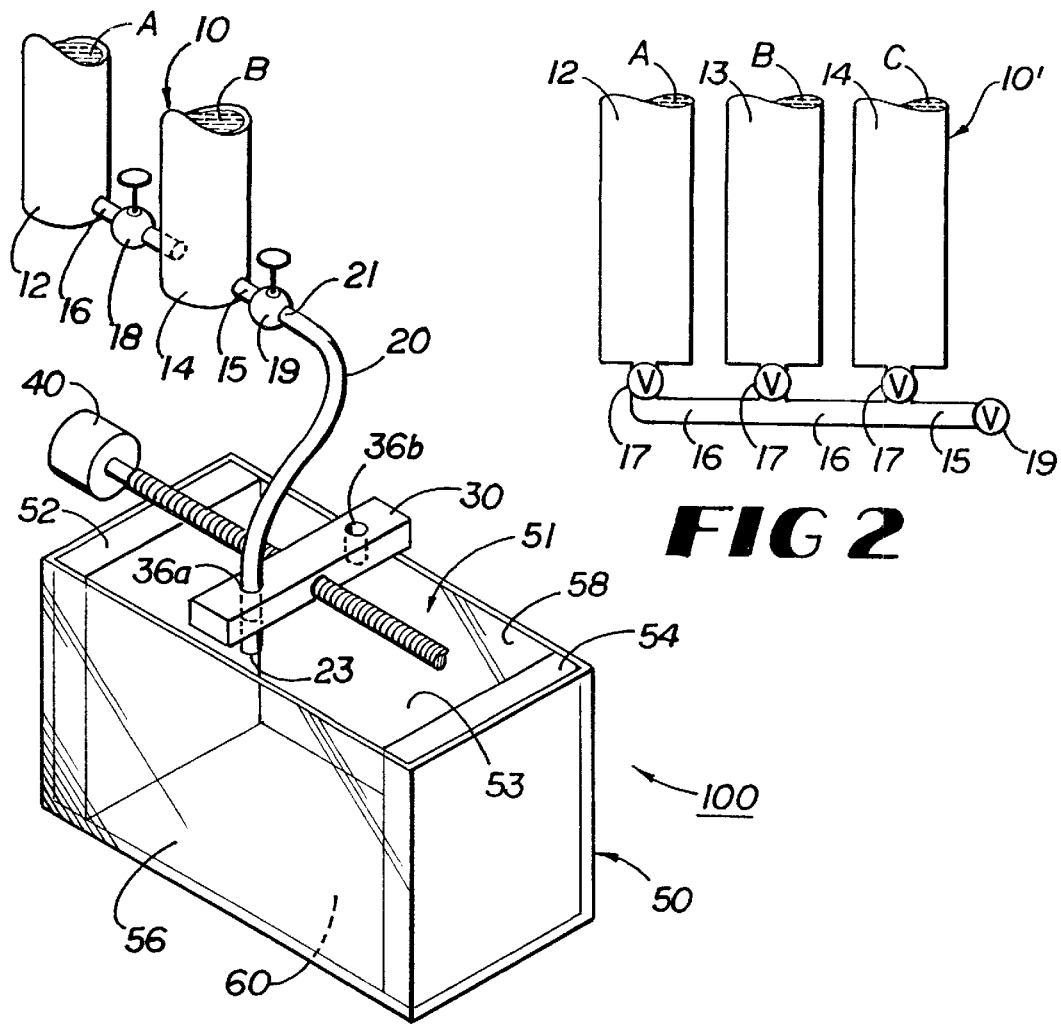
FIG 1
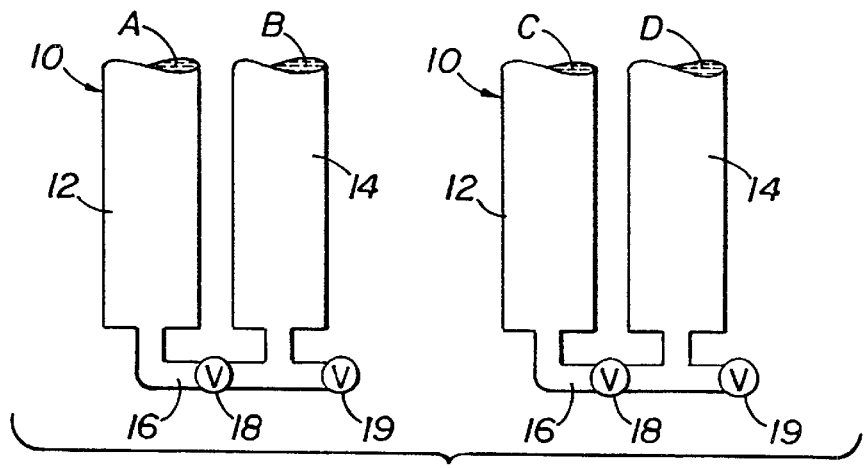
FIG 2
FIG 3

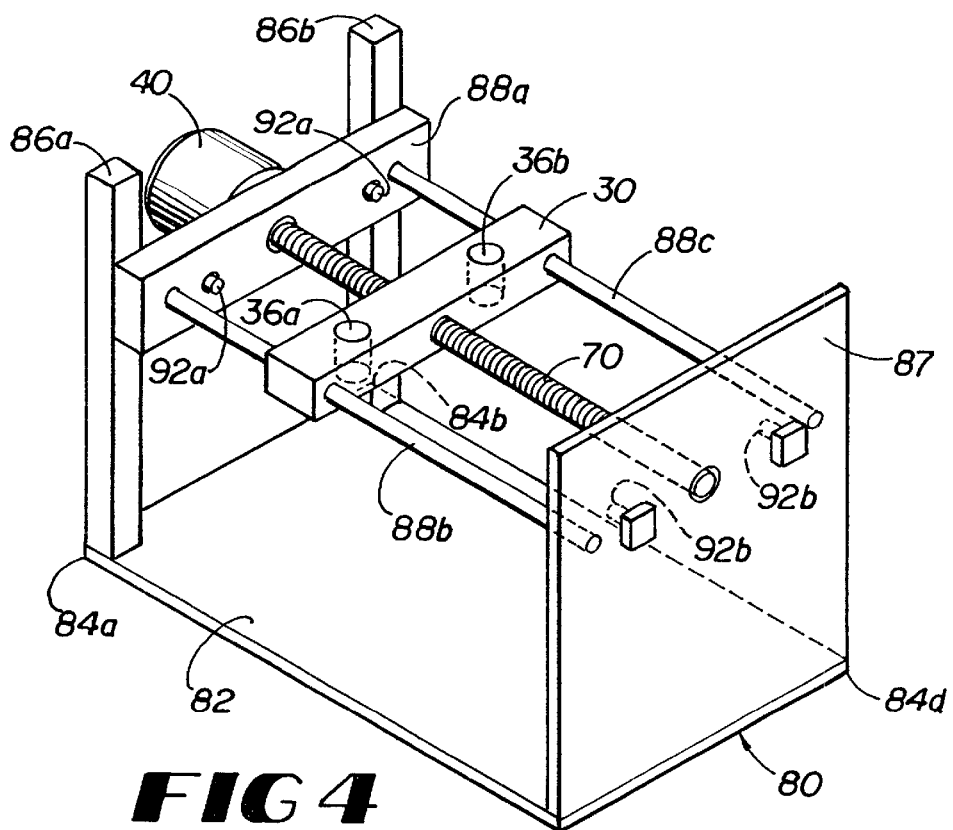
FIG 4
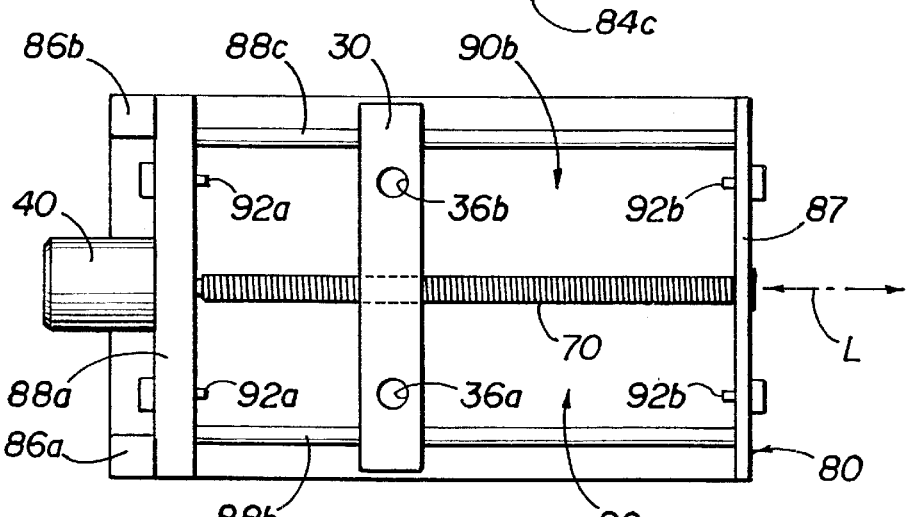
FIG 5
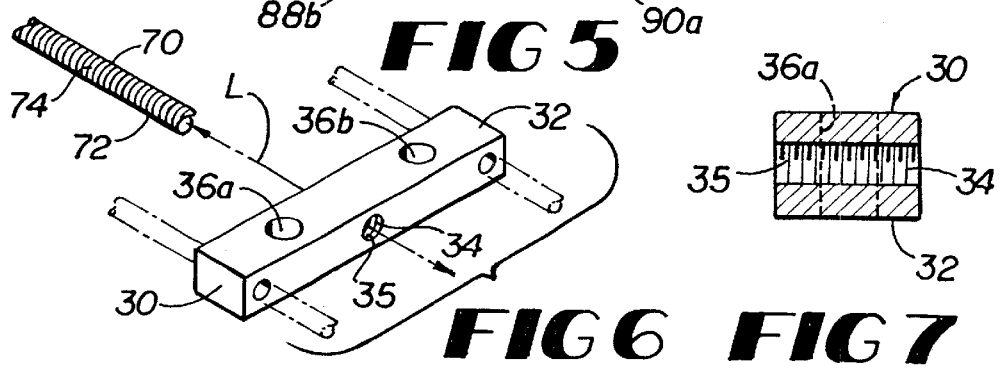
FIG 6  FIG 7

METHOD OF MAKING A GRADIENT GEL WITH A MOVABLE DISPENSING TIP

This application is a divisional application of, and claims benefit of, U.S. application Ser. No. 09/219,402, filed Dec. 23, 1998, now U.S. Pat. No. 6,267,579, the disclosure for which is hereby incorporated herein in its entirety by reference.

BACKGROUND OF THE INVENTION

1. Field of the Invention

The present invention comprises an apparatus and method for making a gradient gel, and more particularly, the present invention relates to an apparatus and method of using a movable dispensing device to form a uniform linear gradient across a wide gel that provides more than twenty sample lanes so that more than forty samples can be analyzed simultaneously with a conventional dual-gel electrophoretic chamber.

2. Background Art

DESCRIPTION OF THE PRIOR ART

Sixty to seventy five percent of the cholesterol in blood is associated with low density lipoproteins ("LDL") which consist of a non-homogeneous mixture of spherical particles ranging widely in particle size (23–28 nm), buoyant density and chemical composition. Using a non-denaturing 2–16% polyacrylamide gradient gel electrophoresis, researchers have noted that individuals with a high-risk lipid profile were most likely to have primarily small, dense LDL particles, as discussed in the paper "Genetic control of low density lipoprotein subclasses," Austin et al., Lancet 2: 592–595(3)(1986). In a case-control study of men and women with documented myocardial infarction (MI) published in the paper "Low-density lipoprotein subclass patterns and risk of myocardial infarction," Austin et al., J. Amer. Med. Assoc. 260: 1917–1921(4) (1988), it was reported that LDL phenotype B, the LDL subclass pattern characterized by a preponderance of small dense LDL particles, was associated with a 3-fold increased risk of MI. This association remained significant after adjustment for age, sex and relative weight. It has also been suggested that there may be a major genetic determinant for this LDL phenotype as in the paper "Inheritance of Low-density lipoprotein subclass patterns: results of complex segregation analysis," Austin et al., Am J Hum Genet 73: 838–876 (5) (1988). Whether or not the relationship between LDL phenotype and CAD is independent of other risk factors such LDLc, HDLc or TRIG is still unclear.

High density lipoproteins (HDL) are responsible for the reverse transport of cholesterol from peripheral tissues back to the liver. Data from the paper "Altered particle size distribution of apoA-I-containing lipoproteins in subjects with coronary artery disease," Cheung et al., J. Lipid Res. 32: 383–397 (1991), and the paper "Characterization of human high density lipoproteins by gradient gel electrophoresis," Johansson et al, Biochim Biophys Acta 665: 708–719 (1991), would suggest that patients with documented CAD may have altered HDL particle size distribution when compared to that observed in non-CAD controls. In these studies, the heterogeneity of plasma HDL was assessed using a non-denaturing 4–30% polyacrylamide gradient gel first described in the paper "Characterization of human high density lipoproteins by gradient gel electrophoresis," Blanche et al., Biochim Biophys Acta 665: 708–719 (1981).

A major impediment to large prospective studies of lipoprotein particle size distribution has been the unavailability of an efficient and reproducible method that can allow the determination of particle diameters for cholesterol-rich lipoproteins. This is mainly because high quality pre-cast gradient gels used in the earlier studies are no longer available commercially. The paper "Production of polyacrylamide gradient gels for the electrophoretic resolution of lipoproteins," Rainwater et al., J. Lipid. Res. 33: 1876–1881 (1992), has reported a procedure for the preparation of a 4–30% gradient gel which provides estimates of HDL particle size comparable to those obtained with the PAA 4/30 gel (Pharmacia). In this gradient, however, LDL and larger lipoprotein particles tend to accumulate at the top of the gel, prohibiting the determination of particle size of these lipoproteins. A custom-made 2–16% gradient gel was also described by these investigators for the determination of LDL particle size in the paper "Effects of diabetes on lipoprotein size," Singh et al., Arterioscl. Thromb. Vasc. Biol. 15: 1805–1811 (1995). Except for Gambert et al., who used lipid staining to visualize the LDL band as disclosed in the paper "Human low density lipoprotein fractions separated by gradient gel electrophoresis: Composition, distribution and alterations induced by cholesteryl ester transfer protein," J. Lipid. Res. 31: 1199–1210 (1990), most investigators used Coomassie to stain the gels for protein after the electrophoresis. The use of a protein stain typically requires extensive staining and de-staining procedures for the gels after electrophoresis and special handling of the gels during these steps to maintain gel size and shape before scanning. Furthermore, by using a protein stain, many protein bands other than those corresponding to plasma lipoproteins are visible from the electrophoresis of whole plasma.

It is very difficult to make high quality of gradient gels for medical studies and clinic use. In the casting of the typical gradient gels, as shown in Rainwater et al. paper, the polyacrylamide solutions are commonly allowed to flow into a gel chamber from a stationary dispensing tip which is typically placed at the center of the gel. However, as the polyacrylamide solution flows from the dispensing tip to the sides of the plate, a secondary gradient is formed across the width of the gel resulting in lower gel concentrations toward the edges because of the diffusion of the solution. In order to reduce this diffusion effect, only narrow gels with 6–8 lanes across have been available to-date although a typical gel chamber is capable of having gels with up to 20 or more lanes. Moreover, uneven gradients and disturbances in the process of gel making due to the diffusion still exist even in the narrow gels.

SUMMARY OF THE INVENTION

Definitions

A number abbreviations used in this application for some frequently used technical terms are defined as the following:

The term "S-GGE" as used herein shall refer to a segmental gradient gel electrophoresis.

The term "S-GGE 2.8/8.30" as used herein shall refer to a 2.8/8.30 segmental gradient gel electrophoresis with a 2–8% gradient stacked above an 8–30% gradient.

The term "LIPOPROTEIN" as used herein shall refer to a class of plasma proteins that are complexed to lipids.

The term "TRIG" as used herein shall refer to triglycerides.

The term "CHOL" as used herein shall refer to cholesterol.

The term "LDL" as used herein shall refer to low density lipoproteins.

The term "HDL" as used herein shall refer to high density lipoproteins.

The term "Lp(a)" as used herein shall refer to lipoprotein (a) which consist of one LDL particle complexed to one apo(a) particle.

The term "LpB" as used herein shall refer to apob-containing lipoproteins.

The term "LDLc" as used herein shall refer to LDL-cholesterol.

The term "HDLc" as used herein shall refer to HDL-cholesterol.

The term "LpA-I" as used herein shall refer to apoA-I containing lipoproteins.

The term "LpA-I/A-II" as used herein shall refer to lipoproteins containing both apoA-I and apoA-II.

Summary

The present invention provides a new apparatus and method for making a uniform gel including a uniform, continuous gradient gel in many lanes occupying up to the capacity of a gel chamber. Moreover, the present invention can be practiced to produce a segmental gradient gel that would provide optimal conditions for the simultaneous characterization of LDL, Lp(a) and remnant lipoproteins (2–8% gradient) and HDL subclasses (8–30% gradient) from whole plasma. Additionally, the present invention allows the bands corresponding to all of the major lipid-carrying particles to be visualized without any handling of the gel. The present invention can also be practiced to make several gradient gels simultaneously. In sum, the present invention offers a new, better, and efficient gel making apparatus and method.

The present invention in one embodiment is a gel-making system that has a reservoir for holding a solution. The reservoir is connected to a movable arm through a tubing. The tubing has two ends: one end is in fluid communication with the reservoir; and the other, an open end, is received by the movable arm. A gel holder having an internal gel chamber is placed underneath the movable arm for receiving the solution. In operation, the movement of the movable arm causes the open end of the tubing to move along with it and the open end of the tubing delivers the solution in motion to the internal gel chamber to form the gel.

In order to make a gradient gel, normally two solutions with different concentrations are used. Accordingly, one embodiment of the present invention employs a gradient maker that consists of a reservoir having a first container and a second container. The first container holds a first solution and the second container holds a second solution. A channel connects the first container and the second container with an outlet connected to the second container and in communication with the channel so that a fluid of the first solution and the second solution is formed at the outlet. A tubing having a first end and a second end connects to the outlet with the first end. The second end of the tubing is received by a movable arm and moves along with the movable arm. A gel holder with an internal gel chamber is placed underneath the movable arm for receiving the fluid, where the chamber has a longitudinal axis. The movable arm moves back and forth along the longitudinal axis so that the second end of the tubing delivers the fluid in motion in the gel chamber to form the gradient gel. In a linear gradient gel the bottom of the gel has a higher concentration and the top of the gel has a lower concentration.

A linear gradient gel can be formed from more than two solutions. In another embodiment of the present invention, a reservoir has a plurality of containers holding a plurality of solutions. Each container holds one solution and communicates with at least one neighboring container. An outlet is connected to at least one container to communicate with the containers so that a fluid of at least two solutions from the plurality of solutions is formed at the outlet. A tubing, having a first end and a second end, is connected to (and is in fluid communication with) the outlet through the first end. A movable arm receives the second end of the tubing and causes the second end of the tubing to move along with it. A gel holder with an internal gel chamber is placed underneath the movable arm for receiving the fluid, where the chamber has a longitudinal axis. The movable arm moves back and forth along the longitudinal axis of the chamber so that the fluid is transferred from the first end to the second end of the tubing and then is delivered in the chamber by the second end of the tubing in motion to form the gradient gel.

In gel making, approximately two hours are required for the gel solution to polymerize and form a solid matrix. One advantage of the present invention is that several highly uniform gradient gels can be made simultaneously. In one embodiment of the present invention, a plurality of reservoirs are utilized. Each of them has a first container and a second container, where the first container holds a first solution and the second container holds a second solution. A channel connects the first container and the second container. Moreover, an outlet is connected to the second container and communicates with the channel. Consequently, a fluid of the first solution and the second solution is formed at the outlet of this particular reservoir. Thus, a plurality of fluids are formed at the plurality of the outlets of the plurality of the reservoirs. Furthermore, a plurality of tubings, each having a first end and a second end, connect in a one to one relationship to the plurality of reservoirs through the connection of the second end of a tubing to the outlet of a reservoir. A movable arm carries at least a plurality of the second ends of the plurality of the tubings. And a plurality of gel holders are positioned in parallel thereby defining a longitudinal axis. Each of the gel holders has an internal gel chamber for receiving the fluid from one of the plurality of the second ends. When the movable arm moves back and forth along the longitudinal axis, each second end of the tubings delivers one of the fluids in motion into one gel chamber to form one gradient gel. As a result, a plurality of the gradient gels are produced.

In order to make an uniform gradient gel, the movable arm moves at a substantially constant rate of motion. While other mechanisms may be used, one embodiment of the present invention uses a motor to drive the movable arm. One advantage of using the motor driving mechanism is that by adjusting the speed of the motor, the rate of motion of the movable arm can be selected. In order to ensure that the same gel concentration is present across the width of the gel, the rate of motion of the moveable arm is adjusted and set according to the width of the gel and the rate of flow of the solution from the reservoir into the gel chamber. For instance, for a wider gel, the rate of motion should be increased to cover a greater distance in the same interval of time. Also, the height of the reservoir relative to the gel chamber can affect the flow rate, which can be readily taken into account when setting the rate of motion of the movable arm. According to the preferred embodiment, the movable arm has an internally threaded bore and the motor controls the motion of the movable arm through a shaft. The shaft has an elongated body with an external thread on the elongated body. The shaft has a longitudinal axis and is rotatable around its longitudinal axis. The shaft can rotate around the longitudinal axis either in clockwise direction or counter-clockwise direction, and the direction of rotation of the shaft is changeable from clockwise to counter clockwise, or vice versa. The external thread on the elongated body is adapted to mate with the movable arm through the internally threaded bore. The shaft operatively connects to the motor. Thus, when the motor causes the shaft to rotate around its longitudinal axis, the movable arm moves along the longitudinal axis because the mating mechanism of the external thread of the shaft with the internally threaded bore of the movable arm. Because the shaft can rotate around the longitudinal axis either in clockwise direction or counter-clockwise direction, the movable arm is able to move along the longitudinal axis both forward and backward. A switching mechanism may be used to control the direction of the rotation of the shaft.

The movable arm in turn receives an open end of the tubing, which connects with the reservoir at the other end, the open end moving with the movable arm. To do so, the movable arm has means for holding at least a portion of the tubing proximate to the open end of the tubing so that at least the open end of the tubing moves along with the movable arm. In one embodiment of the present invention, the holding means is an opening sized to allow the open end of the tubing to pass through but hold at least the portion of the tubing proximate to the open end of the tubing therein. The movable arm may have several openings at different locations to allow several gels to be made simultaneously, or to give a user freedom to set up the user's devices. The openings can also have different sizes to accommodate tubings with different sizes. Alternatively, other holding means, including a clamping device normally used in laboratories such as a clamp, can be used to associate the tubing with the moveable arm.

The tubing is made from a flexible material so that it can move along with the movable arm easily without impeding the flow of the fluid within the tubing. Many materials can be used. In one embodiment of the present invention, tubings made from Manosie silicone rubber by VWR Scientific Products Corporation, located at Willard, Ohio are used. In use, the tubing transfers fluid from the reservoir and delivers the fluid in motion at a substantially constant rate of flow. The tubing may deliver the fluid through a dispensing tip. Or, the fluid can be delivered simply through an open end of the tubing.

Solutions to make a linear gradient gel normally are polyacrylamide solutions. These solutions can be identified as high concentration polyacrylamide solution, medium concentration polyacrylamide solution and low concentration polyacrylamide solution. For a preferred embodiment of the present invention, a solution according to a mixing ratio of a 2.3 g acrylamide and 0.1 g N,N'-methylene-bis-acrylamide in 100 ml of borate buffer is regarded as a low concentration polyacrylarnide solution (2.4%), a solution according to a mixing ratio of a 10.24 g acrylamide and 0.43 g N,N'-methylenebis-acrylamide in 100 ml of borate buffer is regarded as a medium concentration polyacrylamide solution (10.67%), and a solution according to a mixing ratio of a 38.4 g of acrylamide and 1.6 g N,N'-methylene-bis-acrylamide in 100 ml of borate buffer is regarded as a high concentration polyacrylamide solution (40%).

These solutions have been used successfully in the present invention to produce high quality segmental linear gradient gels, namely, a 2–8% continuous linear gradient gel and a 8–30% continuous linear gradient gel. In doing so in one embodiment of the present invention, a commercial gradient maker with a container A and a container B, such as a Hoefer GS 100, purchased from Hoefer Scientific Instr., San Francisco, Calif. is loaded with solutions. Container A and container B connect to each other through a channel. An outlet connects to the container B and communicates with the channel so that a mixed fluid of the first solution and the second solution is formed at the outlet. For this embodiment, the higher concentration of solution is always in container B. To make a 8–30% linear gradient gel, a high concentration of polyacrylamide is in container B and a medium concentration of polyacrylamide is in container A. A tubing transfers the mixed fluid of the high concentration of polyacrylamide and the medium concentration of polyacrylamide from the outlet to a dispensing tip. The dispensing tip can be a separate device. Or an open end of the tubing can function as the dispensing tip. A movable arm receives the dispensing tip. A gel holder having an internal gel chamber with a longitudinal axis is placed underneath the dispensing tip. The motion of the movable arm along the longitudinal axis causes the dispensing tip to move along with movable arm and the dispensing tip delivers the fluid in motion in the gel chamber. Because the motion of the movable arm can be controlled at a substantially constant rate, the fluid can be evenly delivered throughout the gel chamber. Moreover, because the movable arm is capable of traveling the length of the gel chamber, the solution is delivered directly to the gel chamber "on-the-spot." Thus, a secondary gradient resulting from the diffusion of the solution from the dispensing tip to the edge of the gel is not formed. After a proper curing period, a uniform, high quality 8–30% gradient gel is produced. Since in the segmental linear gradient gel a second gel (2–8% segment) must be poured on top of the first gel (8–30% segment), the volume of the solutions is controlled so that the 8–30% gradient gel occupies half space of the gel chamber. As people skilled in the art appreciate, the exact volumes to be placed in the reservoir can be calculated from the dimension of the gel chamber before hand. Furthermore, the entire gel making process according to the present invention can be automated by placing the right volumes of the solutions in the reservoir. The gel is poured to completion until the reservoir is emptied.

The containers A and B are subsequently filled with a medium concentration of polyacrylamide (in container B) and a low concentration of polyacrylamide (in container A) to make a 2–8% gradient gel. The above process is then repeated. And a uniform 2–8% gradient gel is formed on top of the 8–30% gradient gel. As a result, a segmental linear gel consisting of two continuous linear gradients is formed, which can then be used for the simultaneous determination of the diameters of LDL and HDL from whole plasma. The matching of the concentrations at the interface of the two linear gradients in this embodiment provides a continuous transition between the two linear gradients.

In a further embodiment of the present invention, two or more gradient makers, each with two containers A and B, can be used to simultaneously make two or more gradient gels in two or more gel chambers. Therefore, practicing the present invention is economic and efficient, in addition to the advantages of making better continuous gradient gels.

In an additional further embodiment of the present invention, multiple linear gradients can be stacked on top of another to allow optimal separation of the macromolecules of interest. For example, the present invention can be practiced to make a linear gradient gel with three segments. Similarly, gels having other concentration gradients can also be made.

Other objects, advantages and uses for the present invention will be more clearly understood by reference to the remainder of this document.

BRIEF DESCRIPTION OF THE FIGURES OF THE DRAWINGS

FIG. 1 is a schematic view of a gel making system according to the present invention.

FIG. 2 is a schematic view of a first alternative embodiment of the gel making system of the present invention.

FIG. 3 is a schematic view of a second alternative embodiment of the gel making system of the present invention.

FIG. 4 is a partial side view of a gel making system of the present invention.

FIG. 5 is a partial top view of the gel making system shown in FIG. 4.

FIG. 6 is a perspective view of a movable arm according to a preferred form of the present invention.

FIG. 7 is a cross-sectional side view of the movable arm shown in FIG. 6.

DETAILED DESCRIPTION OF THE INVENTION

Figure 8A:
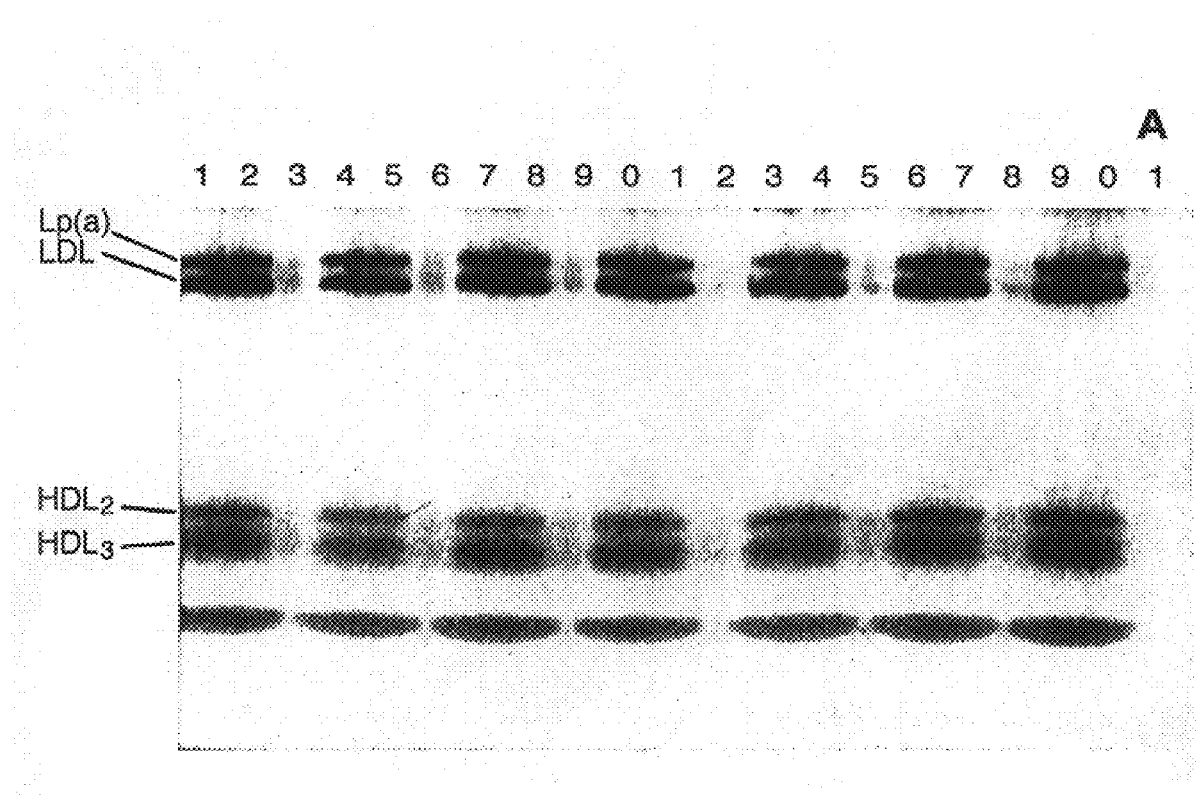
FIG. 8 shows reproducibility of lipoprotein particle size determinations: (A) an actual photograph of a gradient gel with the same plasma sample (CHOL=279, TG=65, HDLc=65 and Lp(a)=175 mg/dL) being applied to 17 of the 21 available lanes. Aliquots of this plasma sample were also applied to different lanes (x-axis) for 5 different gels (different symbols) over a two-week period; (B) the calculated particle diameters (nm) are plotted on the vertical axis as function of lane number (horizontal axis) for each gel and the different symbols represent results from different gels. The mean diameter (-), 1 SD range (---) and 2 SD range (--) are presented for LDL and Lp(a) particle diameter; and (C) same as (B) but for $HDL_2$ and $HDL_3$.
Figure 8C:
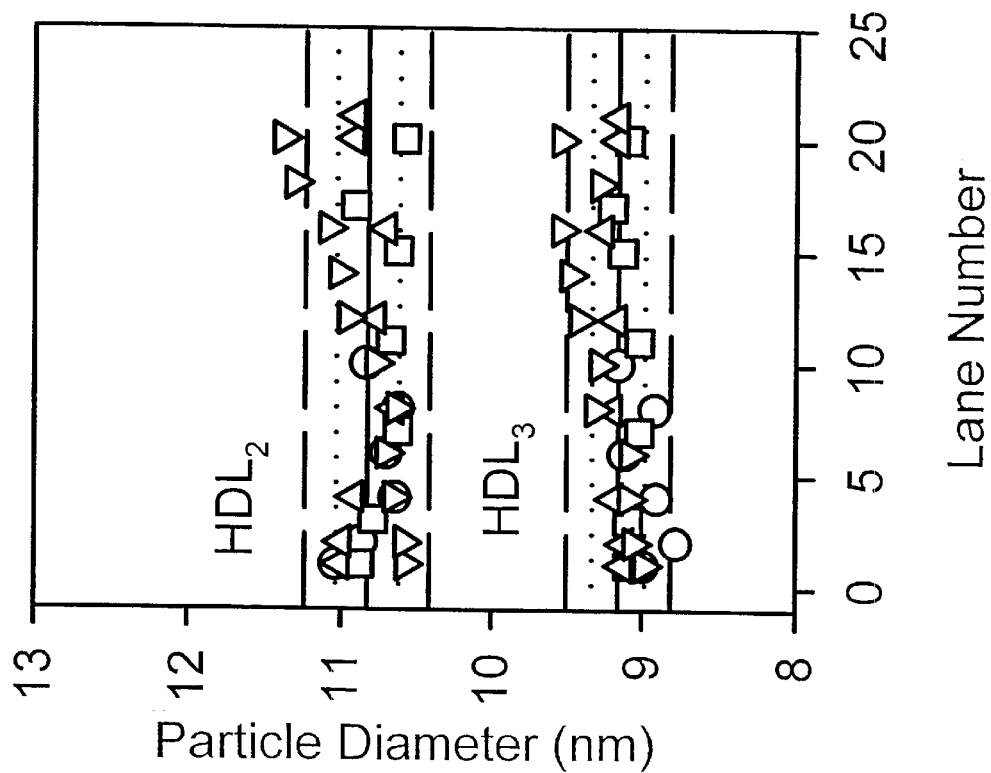

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the FIGS. 1–13, in which like numbers indicate like parts throughout the FIGS. 1–13.

OVERVIEW

Referring generally to FIGS. 1–7, the present invention comprises a gel making system that utilizes a movable dispensing mechanism and method to make high quality gels, especially continuous gradient gels. The present invention allows the reproducible preparation of gradient gels which can be as wide as desired in order to accommodate any number of samples simultaneously. One embodiment of the present invention accommodates up to 21 samples per gel, or 42 samples per run with a dual-gel electrophoretic chamber, compared to several samples per gel using currently available gel making devices. The present invention allows the application of pre-stained plasma samples and the gel can be scanned for particle size immediately at the end of the electrophoretic procedure. Elimination of the extensive staining and de-staining steps after electrophoresis should also minimize the need to handle the gel preventing any artifact that these steps may introduce. Equally important, the use of a lipid stain allows the specific visualization of only the lipoprotein fractions present in whole plasma. Thus, the present invention provides a new device and method to facilitate medical research in the related fields.

Referring now to FIG. 1, the gel making system 100 of the present invention, according to one preferred embodiment, has a reservoir 10 for holding gel making solutions, a tubing 20, a movable arm 30, and a gel holder 50. The reservoir 10 has two containers 12, 14, each of them is used for holding one solution. As shown in FIG. 1, container 12 holds solution A and container 14 holds solution B. The containers 12 and 14 are connected by a channel 16 so that the containers can be in fluid communication to each other. Cross-sectionally, channel 16 can be square, oval, circular or in other geometrical shapes. An optional stopcock or valve 18 may be used to control the fluid communication between the containers 12, 14. Moreover, as people skilled in the art know, the ratio of the cross-sectional dimension of the channel 16 to the cross-sectional dimension of an outgoing channel 15 determines the characteristic of the gradients: a linear gel is generated when they are the same and a nonlinear gel results when they are not.

An outlet 19 is connected to the outgoing channel 15 and communicates with the channel 16 so that a mixture of the solution A and the solution B is formed by the time the solutions reach the outlet. The cross-sectional area of the channel 16 determines how fast solution A in container 12 mixes with solution B in container 14. The location of the outlet 19 is important but variable. In the embodiment shown in FIG. 1, the outlet 19 is connected to the container 14. Alternatively, the outlet 19 can be connected to the container 12. Or the outlet 19 may be connected to both of the containers 12, 14, for example, through the channel 16, at a location near the stopcock 18. The location of the outlet 19 impacts the arrangement of solutions in the containers 12, 14. For the embodiment shown in FIG. 1, container 14 always holds a solution with a higher concentration of polyacrylamide.

Reservoir 10 can have alternative arrangements of containers. FIG. 2 shows one alternative to the embodiment of the reservoir 10 shown in FIG. 1. In FIG. 2, reservoir 10' has three containers 12, 13 and 14, each of them for holding one solution. As shown in FIG. 2, container 12 holds solution A, container 13 holds solution B and container 14 holds solution C. The containers 12, 13 and 14 are connected by a channel 16 and an outgoing channel 15 so that the containers can be in fluid communication to each other. Optional stopcocks or valves 17 may be used to control the fluid communication among the containers 12, 13 and 14 so that a variety of fluids, such as A+B, A+C, B+C, or A+B+C, can be made.

Multiple reservoirs 10 can also be used in the present invention as shown in FIG. 3, where two reservoirs 10 are used to provide capacity for making two gradient gels simultaneously as discussed in detail vide infra.

Still referring to FIG. 1, the tubing 20 has two ends 21, 23. The tubing 20 is connected to the outlet 19 through the end 21 and is in fluid communication with the outlet 19. End 23 is an open end and is received by the movable arm 30.

The movable arm 30, referring to FIGS. 1, 6 and 7, has a body 32 and openings 36a, 36b. Each opening is sized to allow the end 23 of the tubing to pass through and hold at least a portion of the tubing 20 proximate the end 23 of the tubing therein. In the embodiment shown in FIG. 1, the tubing 23 is received by opening 36a. Alternatively, it can be received by opening 36b. If multiple reservoirs are used as shown in FIG. 3, each opening would receive a tubing. The movable arm 30 can have one, or two, or more openings to accommodate the need of a user. Moreover, each opening can be sized differently to accommodate the size of the tubing. Furthermore, cross-sectionally each opening may be circular, square, rectangular, triangular, diamond, oval or other geometrical shape. Accordingly, openings can be cylinders (as shown in FIG. 7), cubic, cone or other geometric shapes. The movable arm 30 can also take different shape. Cross-sectionally the body 32 may be circular, square, rectangular, triangular, diamond, oval or other geometrical shape. Other alternatives can also be used to associate the tubing 20 with the movable arm 30. For example, a clamp (not shown) can be used to associate the tubing 20 with the movable arm 30.

A gel holder 50 is placed underneath the end 23 and the movable arm 30. The gel holder 50 has an internal gel chamber 51 defined by two spacers 52, 54, two glass plates 56, 58, and a bottom 60. The chamber 51 has an open top 53 to allow the fluid to be delivered therein through the end 23 of the tubing 20. The fluid can be delivered into the chamber 51 directly through the open end 23 of the tubing 20. Optionally, a dispensing tip (not shown) can be used to deliver the fluid.

The movable arm 30, in this embodiment, is driven by a motor 40. One advantage of using the motor 40 to drive the movable arm is that by adjusting the speed of the motor 40, the rate of motion of the movable arm can be selected. Once a rate of motion is decided, the motor 40 can keep the movable arm 30 moving at that rate of motion constantly. A wide range of motors may be used. For the preferred embodiment of the present invention, motor 40 is an IG P/N 13556-165730 motor manufactured by Igurashi Electric Works, Japan.

The motor 40 controls the motion of the movable arm 30 through a shaft 70.

According to the embodiment shown in FIGS. 4–6, the movable arm 30 has an internally threaded bore 34. The shaft 70 has an elongated body 72 with an external thread 74. The external thread 74 on the elongated body 72 is adapted to mate with the movable arm 30 through the internally threaded bore 34. The shaft 70 has a longitudinal axis L and is rotatable around its longitudinal axis. The shaft 70 can rotate both clockwise and counterclockwise. The direction of the rotation of the shaft 70 is controlled by switches 92a, 92b. Switches 92a, 92b change the direction of rotation of the shaft 70 from clockwise to counter-clockwise, or vice versa. Switches 92a, 92b may be pressure sensors, optical-electrical device, electromagnetic device or other devices. In this embodiment, switches 92a, 92b are double pole, double throw type 8221 SHZGE switches, which can be found in most hardware stores. The shaft 70 operatively connects to the motor 40. Thus, when the motor 40 causes the shaft 70 to rotate around its longitudinal axis L, the movable arm 30 is driven to move along the longitudinal axis L because the mating mechanism of the external thread 74 of the shaft 70 with the internal thread 35 of the internally threaded bore 34 of the movable arm 30. Because the shaft 70 rotates around the longitudinal axis either in clockwise direction or counter-clockwise direction alternately, the movable arm 30 is able to move along the longitudinal axis forward and backward continuously. Other mechanisms can be used to control the motion of the movable arm 30. For example, an air gauge can be used to drive the movable arm 30. Additionally, electromagnetic mechanism and spring mechanism may also be utilized.

The movable arm 30, the motor 40 and the shaft 70 are supported by a housing 80. Referring now to FIGS. 4 and 5, housing 80 has a horizontal base 82 with corners 84a–d. Two supporting posts 86a, 86b are bearing against the corners 84a, 84b. Crossing then horizontal base 82, a supporting board 87 is bearing against the corners 84c, 84d. Alternatively, supporting board may be replaced by more supporting posts. Moreover, the positions of the supporting board 87 and the supporting posts 86a, 86b are interchangeable. The supporting posts 86a, 86b are connected by a horizontal bar 88a, and the supporting board 87 is connected to the supporting posts 86a, 86b by horizontal bars 88b, 88c. In the embodiment shown in FIGS. 4 and 5, the horizontal bars 88b and 88c are parallel to each other and therefore define a longitudinal axis. The supporting board 87 and the horizontal bar 88a are parallel to each other but perpendicular to the longitudinal axis. Optionally, the horizontal bars 88a–c are movably connected to the supporting posts 86a, 86b and the supporting board 87 so that the heights of the horizontal bars 88a–c relative to the horizontal base are adjustable individually. The shaft 70 connects the horizontal bar 88a and the supporting board 87 and divides the housing 80 into two compartments 90a, 90b. The motor 40 is operatively connected to the shaft 70 and also supported by the horizontal bar 88a. The switches 92a, 92b are mounted on the horizontal bar 88a and the supporting board 87 respectively.

Each of the compartments 90a, 90b can be used to receive a gel holder 50. Or two gel holders 50 can be received at once. Alternatively, by expanding the size of the housing 80 and length of the movable arm 30, more gel holders can be placed within the housing 50 to make gels. Moreover, the height of the movable arm 30 relative to the horizontal base 82 may be adjusted by adjusting the heights of the horizontal bars 88a–c to accommodate gel holders 50 with different heights.

Now the gel making system 100 is ready to be used. Referring now to FIGS. 1, 4 and 5, the solution A from the container 12 and the solution B from the container 14 form a mixture fluid at the outlet 19. The fluid travels through the tubing 20 to the open end 23. The motor 40 is activated to drive the shaft 70 to rotate about the longitudinal axis L. The shaft 70 in turn, by the mating mechanism between the shaft 70 and the movable arm 30, causes the movable arm 30 to move along the longitudinal axis. When the movable arm reaches either switch 92a or switch 92b, the rotational direction of the shaft 70 is changed from clockwise to counter-clockwise, or vise versa. Because the change of the direction of rotation of the shaft 70, the movable arm reverses it's direction of motion along the longitudinal axis as well. As a result, the movable arm moves back and forth between the horizontal bar 88a and the supporting board 87. In a continuous motion, the movable arm travels back and forth along the longitudinal axis and causes the open end 23 of the tubing 20 to move along with it. During this oscillating motion, the open end 23 delivers the fluid into the internal gel chamber 51 through the open top 53 between the two spacers 52 and 54. Because the movable arm 30 moves at a constant rate of motion, open end 23 delivers the fluid in motion at a substantially constant rate of flow. After a proper amount of the fluid is deposited in the gel chamber 51, it can be cured to form the desired continuous gradient gel.

It is possible to make a second gradient gel on top of the newly made gradient gel so that the two gels form a continuous concentration change from the bottom of the first gradient gel to the top of the second gradient gel. To do so, the volumes of the solutions A and B are selected so that the gradient gel is formed at the bottom half of the gel chamber 51. Then the containers 12, 14 are emptied and refilled with two new solutions and the above process is repeated to form a second gel on the top half of the gel chamber 51. Because the fluids are delivered at substantially constant rate of motion and from side-to-side, the upper edge of the first gradient gel is rather smooth so as to support the second gel on the top half. Because the diffusion effect is minimized in the present invention, much wider and better quality gels are produced according to the present invention.

While it is desirable to make a gel up to the capacity of the gel chamber by delivering the fluid in side-to-side motions, an optional stopper can be put on the track of the movable arm 30 to customize the size of the gel to be made. Furthermore, referring to FIGS. 3–5, two or more gel holders can be placed in the housing 80 to simultaneously make multiple gels. The solutions at each reservoir can be same or different, depending on a user's need.

The invention will be better understood by reference to the following illustrative example, which is performed according to the present invention.

EXAMPLES

Materials

Polyacrylamide was obtained from Sigma Chemicals (A-3553 and M-7279), as were the ammonium persulfate (A-1433) and TEMED (T-9281) and the stain, Sudan Black B (Sigma: S-0395). Ethylene glycol (E178-1) and boric acid (BP 168-500) were purchased from Fisher Scientifics. Tris (hydroxymethyl)aminomethane (EK-1174952) was from VWR Scientifics.

Equipment

Some components of the gel apparatus as shown in FIGS. 1–7 were purchased from Hoefer Scientific Instruments at San Francisco, Calif. and included the SE 650 vertical slab unit, the SG-100 gradient maker, and the PS-1500 power supply. The gradient gel was prepared using the 18×8 slab gel unit from Hoefer (SE 6402) with a 3-mm spacer. Two 12-slot sample applicators from Isolabs (GC-50) were adapted for our gel system to optimize sample loading. The gel was scanned using the LKB 222-020 UltroScan XL Laser Densitometer. The oscillating motion of the dispensing arm was controlled by a platform mixer (Vari-Mix, Thermolyne). The movable arm and mating shaft were manufactured in the inventors' laboratory.

Buffers

Three stock preparations containing high, intermediate and low concentrations of polyacrylamide were available: (1) HIGH: 38.4 grams of acrylamide and 1.6 g N,N'-methylene-bis-acrylamide in 100 ml of borate buffer (80 mM boric acid, 90 mM Tris, 3 mM EDTA, pH 8.3) and (2) MEDIUM: 10.24 g acrylaride and 0.43 g N,N'-methylenebis-acrylamide in 100 ml of borate buffer and (3) LOW: 2.3 g acrylamide and 0.19 g N,N'-methylene-bis-acrylamide in 100 ml of borate buffer. A stock solution of TEMED was prepared by combining 0.6 ml of TEMED and 99.4 ml of the borate buffer. Ammonium persulfate solution (5 mg/ml) was also prepared with the borate buffer. Preparation of Segmental Gradient Polyacralamide Gels (S-GGE 2.8/8.30) The segmental polyacrylamide gradient gel (3 mm thick) was poured in two steps using the Hoefer SE 6402 gel maker kit with 18×8 cm glass plates and the gradient maker (Hoefer GS 100). Each container of the gradient maker was filled with a mixture of 6 ml of the appropriate polyacrylamide concentration, 1 ml of TEMED buffer and 1 ml of ammonium persulfate solution. For the first stage, the two containers held contained the high (Container B) and medium (Container A) concentrations of polyacrylamide to generate the 8–30% gradient. As shown in FIG. 1, the polyacrylamide solutions were allowed to flow continuously as the movable arm was moved from side to side along the upper rim of the glass plates, thus creating multiple tracks along the glass plates across the width of the gel chamber. This motion (15 side-to-side oscillations/min) ensured the even distribution of the polyacrylamide solution between the plates over the entire width of the gel (14 cm). The containers were allowed to empty completely creating the lower gradient gel (approximately 3.8–4 cm in height) which was then allowed to polymerize at room temperature (2 hours). The containers of the gradient makers were subsequently filled with the medium (container B, 6 ml) and low (container A, 6 ml) concentration polyacrylamide to form the 2–8% linear gradient gel. To each container, 1 ml of TEMED buffer and 1 ml of ammonium persulfate solution were added for a total of 16 ml for both chambers. The quality and reproducibility of the gel is optimal if the rate of gel flow is matched to the appropriate rate of movement of the dispensing arm. The rate of flow is controlled by the mating mechanism between the shaft 70 and the movable arm 30 movable with a mean rate of 1.5 ml/min and the moving arm moved at a rate of 15 cycles/min.

Electrophoresis

Whole plasma (30 μl) was mixed with 10 μl of a prestaining solution (0.6% Sudan Black B solution in ethylene glycol) prior to application to the gel. After a 2-hour incubation period at room temperature, a single load of 10 μl of prestained plasma solution was applied to individual troughs, characteristic of the GA-50 sample applicator (Isolabs). Electrophoresis was performed at room temperature, 50 mA, 80 V for 18–20 hours. Alternatively, the gel image can be digitized using the Image Master Video Documentation System and Analysis Software, which is commercially available.

Calibration of Lipoprotein Particle Size

Whole plasma from a human donor exhibiting distinct lipoprotein bands corresponding to LDL, Lp(a), $HDL_2$ and $HDL_3$ (CHOL=297, TG=97, HDLc=73 and Lp(a)=29 mg/dL) was run in multiple lanes of each gel. The diameter of the LDL band in this plasma sample was calibrated using a set of in-house LDL calibrators (27.7, 25.3 and 24.2 nm). The diameters for the in-house LDL calibrators had been previously standardized against the calibrator pool ILH containing LDL with diameter of 29.7, 27.1 and 24.7 nm available from Dr. Krauss (Donner Laboratory) as previously reported (16,17) using PAA 2/16 gels from Isolabs.

As with other gradient gel systems, the diameters of $HDL_2$ and $HDL_3$ in the SGGE 2.8/8.30 gradient gel were determined using the high molecular weight calibrators obtained from Pharmacia (HMW 17-0445-01). For these calibration runs, the gels were stained for protein with Coomassie after electrophoresis to visualize the protein bands corresponding to the molecular weight standards. The high molecular weight calibrators included: thyroglobulin (17.0 nm), ferritin (12.2 nm), catalase (10.4 nm), lactate dehydrogenase (8.4 nm), and albumin (7.1 nm). Frozen aliquots of plasma from this donor were maintained at −80° C. (up to 2 years) and included in all subsequent runs as calibrators for the gel. The quality of the calibrators was assessed by the actual position of the bands as well as the values calculated for the gel constant. These aliquots were thawed once for each use and discarded without being re-frozen for later use.

Determination of Particle Size using the Gel Constant

From gel chromatography experiments, it is known that the pore size ($S_{pore}$) of polyacrylamide gel varied inversely to the monomer concentration ($T_{gradient}$) i.e.

$$S_{pore}=K_1[1/T_{gradient}] \quad [\text{Eq. 1}]$$

where $K_1$ denotes the unknown proportionality constant. For a linear gradient, the monomer concentration $T_{gradient}$ of the polyacrylamide at any distance d in the gel is a function of the distance d from the top of the gel, thus $$T_{gradient}=f(d). \quad [\text{Eq. 2}]$$

The function f will also depend on the range and slope of the gradient. By combining Equations 1 and 2, we obtained:

$$S_{pore}=K_1 \times [1/f(d)] \quad [\text{Eq. 3}]$$

When gradient electrophoresis is carried out to completion, spherical particles of uniform size will continue to migrate until they reach a distance in the gradient, $d_{particle}$, where the pore size of the gel matrix becomes so small as to prevent further penetration by the particle. At this point of equilibrium the pore size is approximately equal to the particle size. In other words, $$S_{particle}=S_{pore}=K_1 \times [1/f(d_{particle})] \quad [\text{Eq. 4}]$$

or $$C_{gel}=S_{particle} \times f(d_{particle})=S_{pore} \times f(d_{particle}) \quad [\text{Eq. 5}]$$

By using a calibrator of known particle diameter $S_{calibrator}$ and by measuring the distance $d_{calibrator}$ migrated into the gel of this calibrator, we can calculate the gel constant, $C_{gel}$, for this particular linear gradient.

$$C_{gel}=S_{calibrator} \times f(d_{calibrator}).$$

Using the distances determined by the gel scanner for the bands corresponding to the LDL, Lp(a), $HDL_2$ and $HDL_3$ calibrators, we can calculate the gel constants for the upper and lower gels. Since the distance $d_{calibrator}$ depends ultimately on the polyacrylamide concentration in the gel gradient, Eq. 5 would indicate that $C_{gel}$ will depend only on the pore size and should, in theory, be the same independent of the gradient:

$$C_{gel}\text{ (nm-\%)}=S_{calibrator} \times [L+(d_{calibrator})^*(\text{Slope}_{gradient})] \quad [\text{Eq. 6}]$$

where $S_{calibrator}$ is the known diameter (nm) of the calibrator

L is the lowest gel concentration for the gradient, i.e. 2% for the 2–8% gradient and 8% for the 8–30% gradient $d_{calibrator}$ (mm) is the position of the band corresponding to the calibrator from the top of the gradient Slope$_{gradient}$ is the slope (% per mm) of the gradient, or the difference between the lowest and the highest gel concentrations (6% for the top gradient and 22% for the bottom gradient) divided by the height of the gel. The actual height of each gradient can be determined by the operator for each gel using the scanner.

2–8% gradient: with Lp(a) $C_{gel}$=30.40×[2+(9.8)*(6/35)]= 111.863 with LDL $C_{gel}$=25.70×[2+(13.7)*(6/35)]=111.748

8–30% gradient with HDL$_2$ $C_{gel}$=11.80×[8+(38.40–35.0)*(22/37)]=118.255 with HDL$_3$ $C_{gel}$=9.60×[8+(41.70–35.0)*(22/37)]= 115.044

From this estimate of the gel constant, the diameter $S_{unknown}$ of any particle can be calculated from the distance $d_{known}$ from the top of the gel. It should be noted that the densitometer gives the position of the band as referenced to an arbitrary set point (typically, from the edge of the glass plate) and the distance to the top of the gradient must be subtracted to obtain the true distance of migration into the gel. Furthermore, for the lower gradient gel, the actual height of the upper gel must also be subtracted:

$$S_{unknown} = C_{gel}/f(d_{unknown}).$$

With each gel, the calibrator plasma containing Lp(a), LDL, HDL$_2$ and HDL$_3$ of known particle diameters was always applied in 3 separate lanes including the two outside lanes and one toward the center of the gel. From the previously determined diameters of Lp(a) and LDL in the calibrator plasma, 6 separate estimates (2 calibrators×3 lanes) were obtained for the gel constant of the 2–8% gradient. The mean value was used to determine the diameters of LDL and Lp(a) in the unknown samples. Similarly, the diameters of HDL$_2$ and HDL$_3$ in the calibrator plasma allowed the calculation of 6 estimates for the gel constant corresponding to the 8–30% gel gradient and the mean value was used in calculating the HDL particle diameter.

Lipoprotein Isolation

To examine the characteristics the different class of lipoproteins in this system, individual fractions were isolated by ultracentrifugation from freshly collected plasma. VLDL was recovered in the supemate of the 1.006 spin (24-hr spin at 39,000 RPM and 10° C.) using the SW 40 Swinging bucket rotor (Beckman Instruments, Palo Alto, Calif.). LDL was recovered in the density range of 1.019–1.063 gm/ml by sequential ultracentrifugation. Lp(a) was isolated by density ultracentrifugation using a modification of the method reported in the paper "Physico-chemical properties of apolipoprotein(a) and lipoprotein(a-) derived from the dissociation of human lipoprotein(a)," Fless et al., J. Biol. Chem. 261: 8712–8718 (1986). In brief, 1 ml of plasma was adjusted to a density of 1.050 gm/ml using solid KBr and layered with 12 ml of a 1.040 density solution. Ultracentrifugation was performed at 35,000 RPM for 15 hrs (10° C.) using the SW 40 swinging bucket rotor. The fraction corresponding to Lp(a) was removed by careful aspiration and confirmed by ELISA.

In order to compare our estimates obtained for HDL-sized particles with this new procedure, we used LpA-I and LpA-II/A-II fractions which had been isolated by immunoaffinity chromatography as discussed in the paper "Altered particle size distribution of apoA-I-containing lipoproteins in subjects with coronary artery disease," Cheung et al., J. Lipid. Res. 32: 383–397 (1991) and generously donated by Dr. Marian Cheung of the Northwest Lipid Research Laboratory. The diameters of the major protein fractions in these HDL subclasses had been determined using the 4–30% gel available from Alamo Gels, Inc (San Antonio, Tex.). By using these purified HDL subfractions to compare the estimates of particle diameters obtained by the two gels we can be sure that only peaks corresponding to HDL proteins are visualized after staining with Coomassie.

Results

Reproducibility of the S-GGE 2.8/8.30 for Lipoprotein Particle Diameter

Figure 8B:
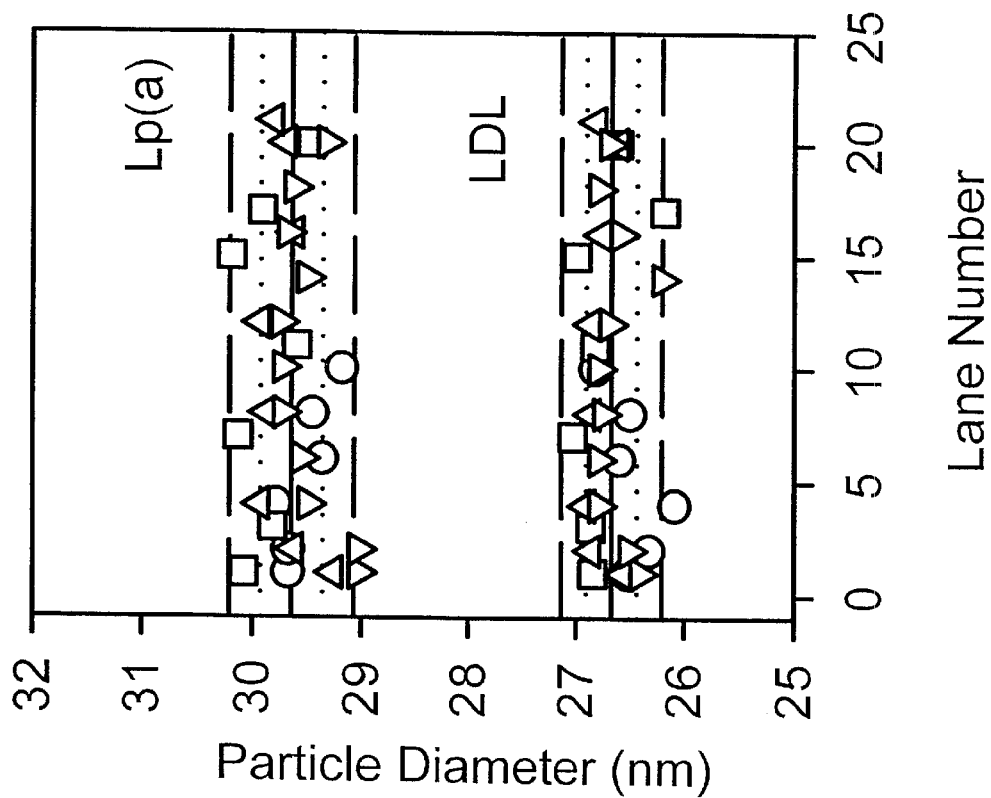

FIG. 8A illustrates the reproducibility of the linear gradient across the 21 lanes of the gel as demonstrated by identical distances of migration across all lanes for all four major lipoprotein bands. FIG. 8B presents the actual particle diameters for obtained for LDL and Lp(a) when the calibrator plasma was applied in multiple lanes of 5 different gels. Only 9.4% (3/32) of the individual particle diameter estimates for LDL were outside 1 SD of the mean and none were outside 2 SD. For Lp(a), 12.5% (4 out of 32 lanes) of the particle diameter estimates from 5 separate gels were outside 1 SD of the mean. None were outside 2 SD. For the HDL subfractions, 18.8% (6 out of 32 lanes) were outside 1 SD and 6.2% (2 out of 32) were outside 2 SD (FIG. 2C). Table 1 presents the mean values and fractional standard deviation (100×SD/Mean) for the distance from the top and for the calculated particle diameter for Lp(a), LDL, HDL$_2$ and HDL$_3$ from 16 lanes on the same gel (within run) as well as values from 65 different gels (between runs).

The reproducibility of the gel constants (mean+SEM for the most recent series of 100 gels) was obtained for both the 2–8% ($C_{gel}$=113.5+0.45) and the 8–30% linear gradients ($C_{gel}$=116.43±0.28). There was no statistical difference between the two estimates for the $C_{gel}$ from the lower and upper gradient gels as assessed by un-paired t-test. These empirical results further support the earlier observation that the pore size at any point in a linear gradient is defined solely by the gel concentration, independent of the range of the gradient prepared.

Figures 9A, 9C:
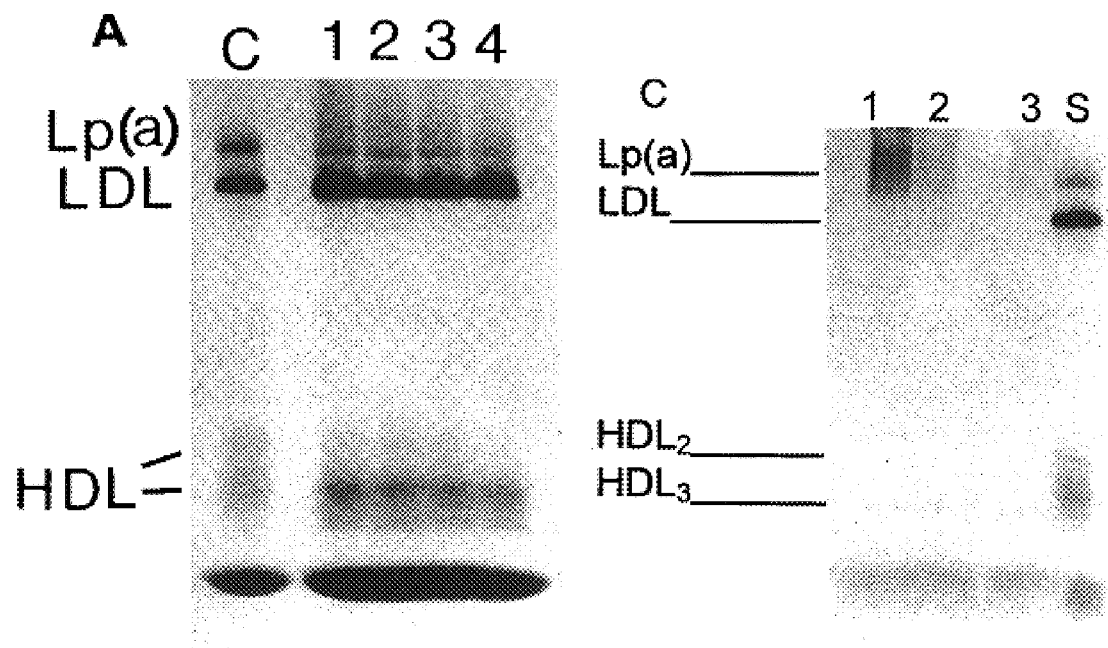
FIG. 9 identifies conditions for optimal lipoprotein bands on the S-GGE 2.8/8.30 gel ('S' indicates the lane to which the Standard (calibrator) sample was applied): (A) by varying the incubation period for pre-staining of whole plasma from 120 min (Lane 1), 60 min (Lane 2), 30 min (Lane 3) to 15 min (Lane 4) it is showed that there was no effect on the position of the Lp(a), LDL, $HDL_2$ and $HDL_3$ bands; (B) the position of the LDL band was not affected by the concentration of LDLc in the 10 µl of sample applied to the lane. A concentrated preparation of LDL (LDLc=270 mg/dL, Lane 5) isolated by ultracentrifugation was dialyzed against normal saline (d: 1.006 and 0.01% EDTA) and diluted with d: 1.006 density solution containing 0.01% EDTA to various concentrations of cholesterol ranging from 160 (Lane 1), 80 (Lane 2), 50 (Lane 3), to 40 (Lane 4) mg/dL. All diluted samples were pre-stained by incubation at room temperature for 2 hours; and (C) the application of comparable concentrations of cholesterol in the form of VLDL resulted in considerably broader bands which are less intensely stained as compared to LDL and Lp(a). VLDL was isolated by ultracentrifugation and applied at cholesterol concentrations of 100 mg/dL (Lane 1, ~530 mg/dL of TG), 50 mg/dL (Lane 2, 265 mg/dL of TG) and 25 mg/dL (Lane 3, 133 mg/dL of TG).

In order to examine the effect of the pre-staining procedure on the electrophoretic mobility of the lipoproteins, whole plasma aliquots from a single donor were incubated in the staining solution for 15 min, 30 min, 1 hr and 2 hrs at room temperature and electrophoresed in adjacent lanes. As shown in FIG. 9A, there was no change in the position of any bands corresponding to the 4 major lipoprotein fractions. Table 2 presents the actual particle diameters for 6 separate incubations at 15 min, 1 hour and 2 hour for a freshly collected plasma sample which displays all 4 major lipoprotein bands. There was no statistical difference in particle size with the different incubation times.

Figure 9B:
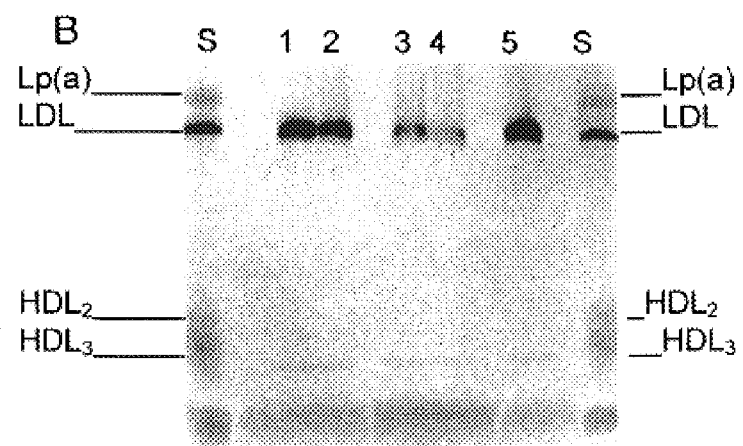

FIG. 9B illustrates the reproducibility of the position of LDL bands as different concentrations of LDLc were applied. With the present protocol for pre-staining and electrophoresis, particle size determination for LDL can be determined from a sample with an LDLc concentration of 40 mg/dL. While there appeared to be a dose-dependence between LDLc and the intensity of the stained LDL bands, we were not able to establish a reliable standard curve between the areas under the LDL peaks as determined from the densitometer and the concentrations of LDL when plasma samples from different donors were analyzed. This is in contrast to the reported data obtained with protein staining. Differences in the lipid composition of LDL among individuals could account for the variability in the stain intensity for different preparations of LDL.

In contrast to the sharp bands characteristic of LDL, small VLDL can be shown to have significantly broader peaks which are poorly stained (FIG. 9C). For this experiment, VLDL from a normotriglyceridemic donor (CHOL=195, TG=80, HDLc=56 and Lp(a)<0.1 mg/dL) was isolated by ultracentrifugation using the SW40 swinging bucket at density d<1.006 gm/ml. In contrast to the band corresponding to 40 mg/dL of LDLc (Lane 4, FIG. 9B), the band corresponding to 50 mg/dL of VLDL-cholesterol (Lane 3, FIG. 9C) was barely visible under identical staining conditions. As shown, the band corresponding to VLDL from this normotriglyceridemic individual was slightly larger than Lp(a) in our calibrator (Lane S) and was significantly more heterogeneous as indicated by the broadness of stained band. In our hands, VLDL isolated by ultracentrifugation of whole plasma obtained from individuals with fasting TG of 350 mg/dL or greater can be visualized as a dark stain at the top of 2% gel suggesting that these particles were too large to enter the gel matrix. Using the value of gel constant calculated for the 2–8% gel and Eq. 6, we would predict that only particles with diameter less than 55 nm would be able to enter the gradient.

Identification of Lp(a)

The identity of the Lp(a) band was confirmed by several approaches. First, the stain characteristics of the Lp(a) band are different from that of VLDL (FIG. 9C). The Lp(a) band is sharper and more comparable to that of LDL than that of VLDL. Secondly, isolated fractions of Lp(a) can be shown to correspond to distinct peaks upon electrophoresis in the S-GGE 2.8/8.30 gel with migration distance identical to the corresponding peaks obtained with whole plasma (FIG. 10). And thirdly, analysis of postprandial plasma samples from an individual demonstrated that the peak corresponding to Lp(a) was unchanged while the area under the peak corresponding to remnants increased at 2 hours postprandially before returning to fasting level after 10 hours (FIG. 11).

Figure 10A:
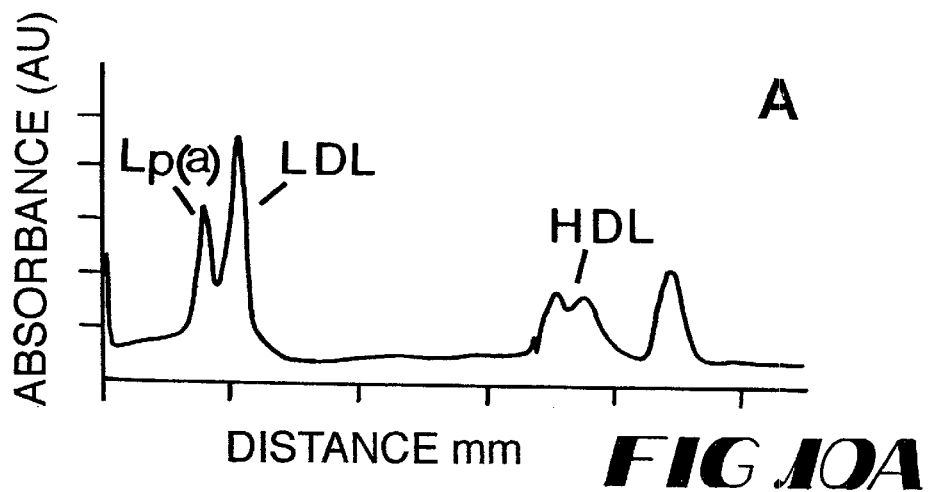
FIG. 10 shows gel scans for whole plasma, isolated Lp(a) and isolated LDL, where Plasma from a healthy normal control woman (CHOL=279, TG=65, HDLc=65, and Lp(a)=175 mg/dL) was used for this experiment: (A) two sharp and distinct peaks can be visualized corresponding to lipoprotein particles with diameters of 23 nm or greater. In view of the low plasma TG and high Lp(a) levels in this individual, we postulated that this peak of larger diameter corresponded to Lp(a); (B) By density gradient ultracentrifugation, a fraction enriched in Lp(a) was isolated and confirmed by ELISA. Upon electrophoresis, this fraction exhibited a major band at the same position as the 'designated Lp(a)' when whole plasma was used. There was a minor peak of small LDL which can be visualized. This would be consistent with contamination by LDL of the Lp(a) fraction which was isolated at a density higher than plasma LDL; and (C) LDL isolated in the density range d: 1.020–1.063 from the same plasma exhibited a single peak corresponding to the major LDL peak seen with whole plasma.
Figure 10B:
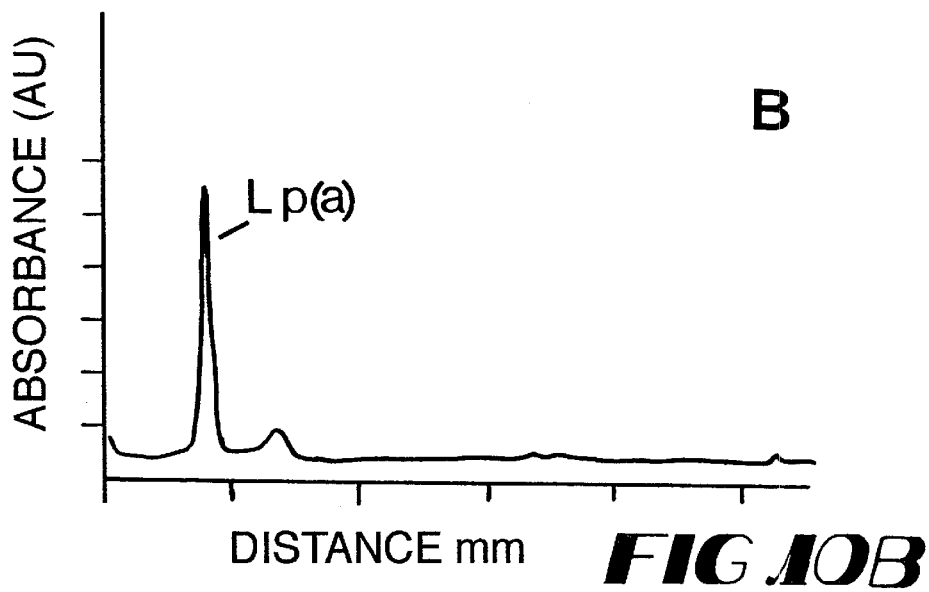
Figure 10C:
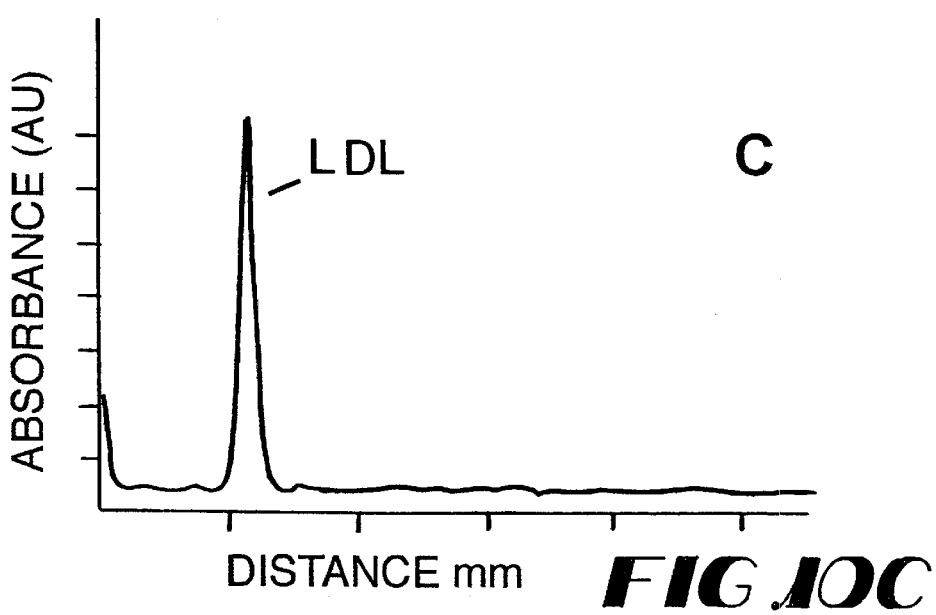

FIG. 10A illustrates actual gel scans for a plasma sample with a high concentration of Lp(a). In FIG. 10B, we present the gel scan of a partially purified Lp(a) isolated by density gradient ultracentrifugation using the SW40 swinging bucket as previously described by Fless et al. paper. The position of the Lp(a) peak was 28.20 mm in whole plasma as compared to 28.52 mm for the isolated Lp(a) from the edge of the plate. This corresponds to a distance of 8.2–8.5 mm from the top of the gel gradient. The gel scan in FIG. 10C illustrates a single peak for LDL isolated by ultracentrifugation in the density range 1.020–1.063 g/ml from the same plasma. In all samples with Lp(a) concentrations of 35 mg/dL or greater as determined by ELISA, we have consistently been able to visualize a band at approximately 8.2–8.75 mm from the top of the gel corresponding to a particle diameter in the range of 27 to 30 nm.

Figure 11A:
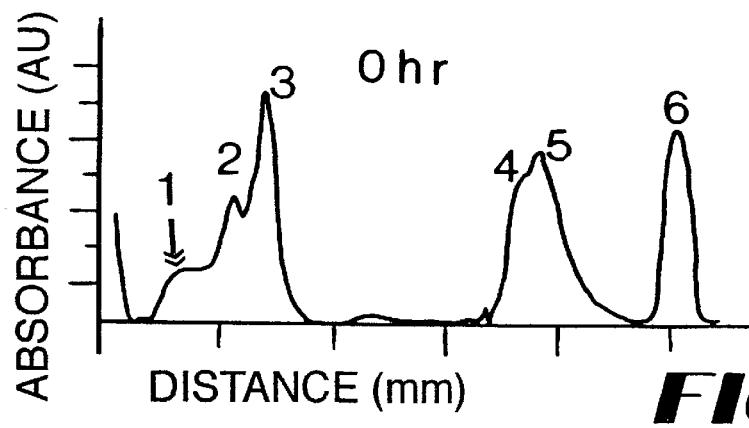
FIG. 11 shows gel scans of whole plasma samples obtained at different times following the consumption of a fat-containing meal: (A) analysis of fasting plasma from a female patient with documented CAD (Lp(a)=85, CHOL=175, TG=125, HDLc=79 mg/dL). In addition to the peaks corresponding to Lp(a) (Peak 2), LDL (Peak 3), $HDL_2$ (Peak 4), $HDL_3$ (Peak 5) and albumin (Peak 6), this sample had a prominent shoulder (Peak 1) to the left of the Lp(a) peak suggestive of the presence of larger lipoproteins; (B) same as (A) but after 2 hours showing a well-defined peak; (C) same as (A) but after 4 hours; (D) same as (A) but after 10 hours, showing Peak 1 became more of a shoulder to the left of the Lp(a) peak as was the case with the fasting plasma sample. This broad peak is believed larger than Lp(a) represents TG-rich remnants. The diameter of Peak 1 is estimated at 36.7 nm with a range of 32 to 39 nm in different samples.
Figure 11B:
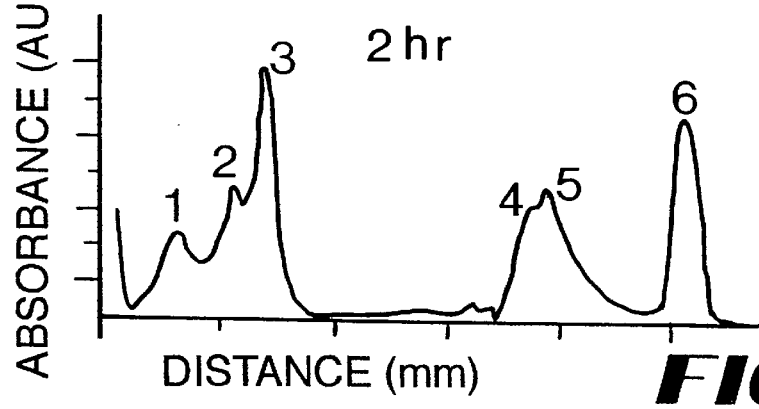
Figure 11C:
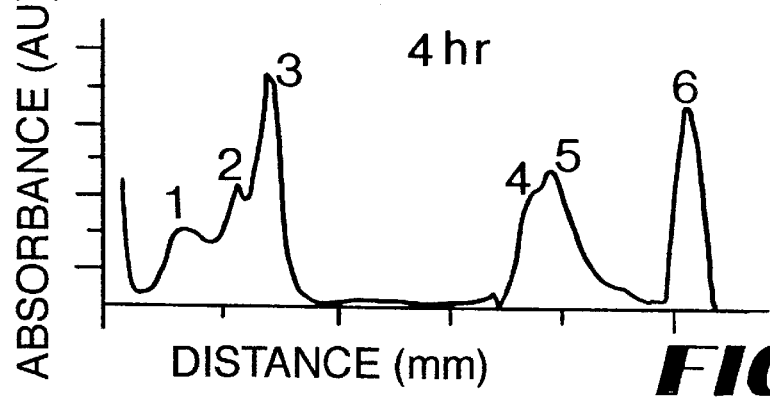
Figure 11D:
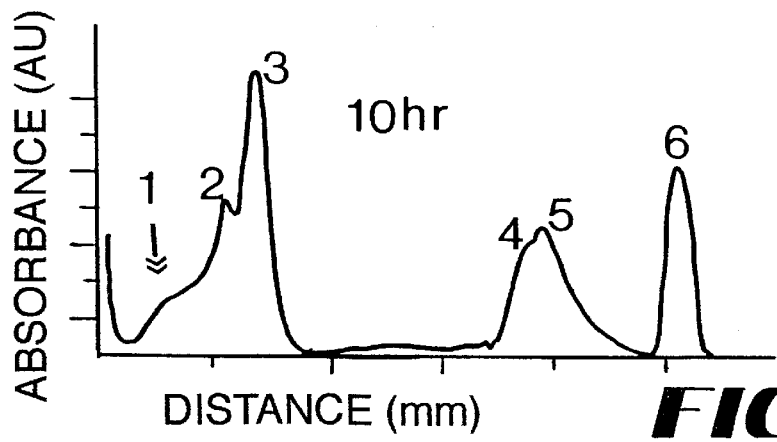

To further demonstrate the ability of the gel to resolve small VLDL and remnants from Lp(a), we examined non-fasting plasma from an individual with a distinct Lp(a) band present in fasting plasma (FIG. 11A). As shown in FIG. 11A, a distinct peak corresponding to Lp(a) was noted that was slightly larger than LDL and a subpopulation of even larger particles appeared as a shoulder (Peak 1) to the left of the Lp(a) peak. Peak 1 was not visible in the gel scans from the plasma of most individuals with normal TG levels (<100 mg/dL, FIG. 10). Postprandial plasma samples collected following the consumption of a standardized liquid test meal containing fat and cholesterol (19,20) were subjected to electrophoresis (FIGS. 11(B)–(D)). At 2 and 4 hours following the test meal, when postprandial plasma TG were expected to increase, this shoulder associated with larger lipoprotein particles clearly became a distinct peak (Peak 1) with increasing areas (FIGS. 11B and C). The position of this band, i.e. the diameter of this lipoprotein fraction, is not changed in postprandial plasma. By 10 hour after the test meal, as plasma TG returned to fasting level, this band of larger lipoprotein particles was reduced back to a shoulder to the left of the Lp(a) peak (FIG. 11D). The particle diameter corresponding to this peak is estimated to be 36.7 nm. We postulate that this peak of larger lipoproteins corresponded to TG-rich lipoproteins and their remnants which were generated during postprandial lipemia. This shoulder is demonstrable in only a subset of the individuals studied with the oral fat load and its presence does not appear to be associated with fasting TG levels. Additional experiments are ongoing to further characterize the nature of this lipoprotein peak. It is clear, however, that the sharp band in the size range from 27 to 30 nm must correspond to Lp(a) and not to IDL or other TG-rich remnant lipoproteins which would typically have larger diameters ranging from 33.5 to 39 nm.

HDL Particle Size: Comparison with SFBR 3/31 Gel

Figure 12A:
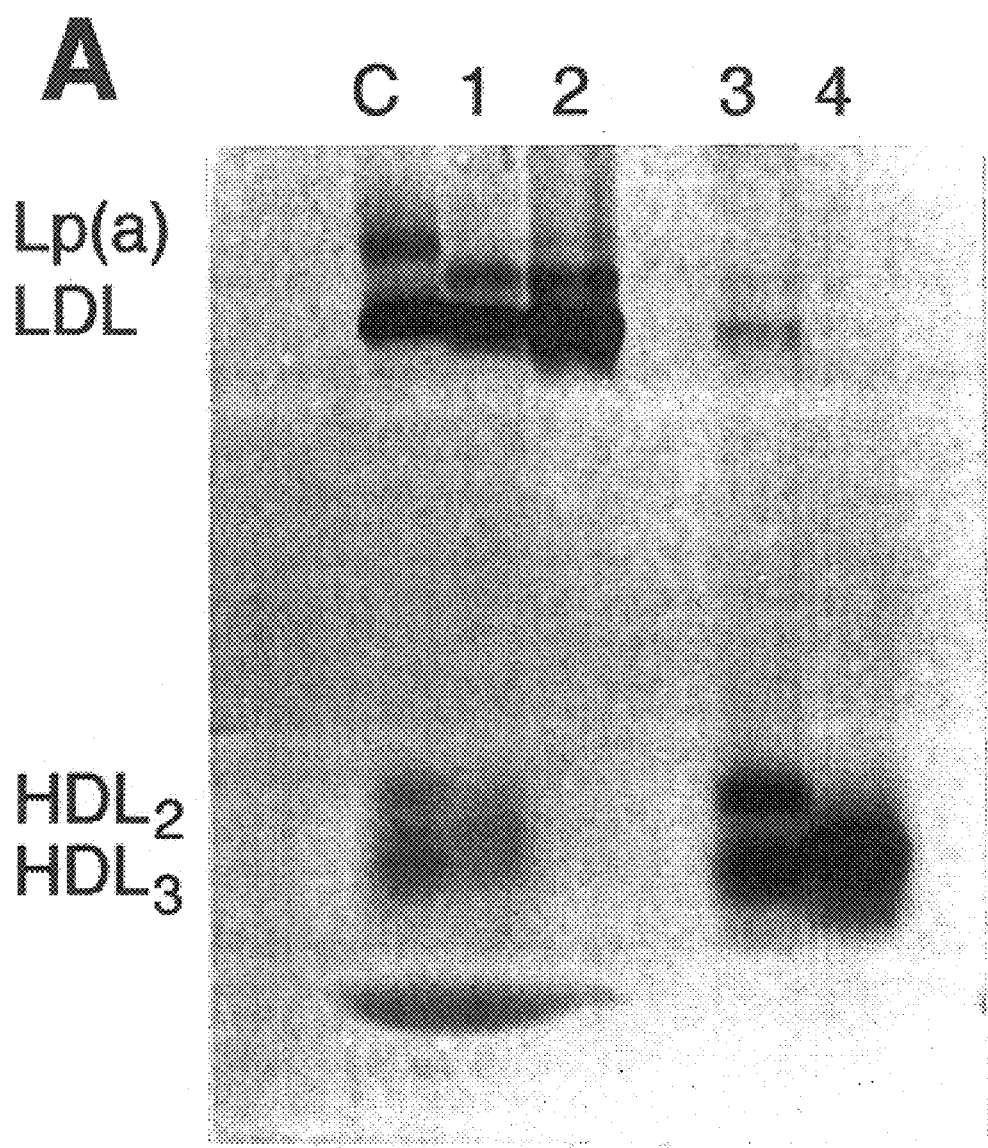
FIG. 12 shows comparison of HDL particle size with the SFBR 3/31 gel system: (A) displays a photograph of a gradient gel depicting the calibrator (Lane 1), whole plasma (Lane 2), LpB (Lane 3), LpA-I (Lane 7) and LpA-I/A-II (Lane 5) for one subject. The band in Lane 7 identified in the size range of plasma LDL does not contain apoB as determined by ELISA and can be shown by FPLC to contain phospholipids, cholesteryl esters, cholesterol, apoE and apoC's (data not shown); (B) shows correlation between HDL diameters determined by protein staining using the SBFR 3/31 gel from Alamo Gels Inc. and by lipid staining using the S-GGE 2.8/8.30 gel after the diameters of the HDL calibrators were adjusted to be comparable with the values reported by Northwest Lipid Research Laboratory. The triangles (D) correspond to peaks identified from LpA-I fractions and the circles (O) indicate peaks identified from LpA-I/LpA-II fractions.
Figure 12B:
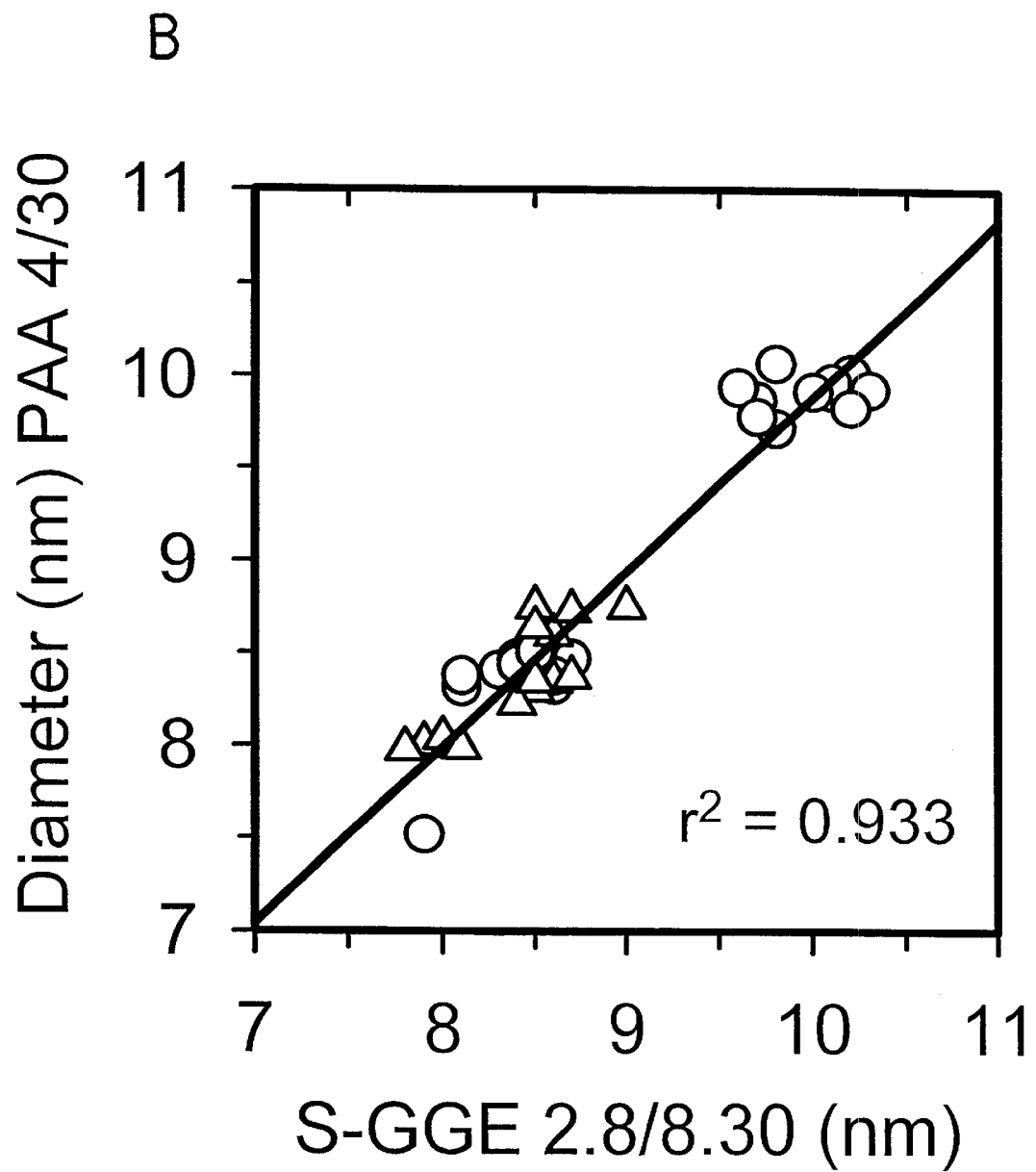

In order to compare the diameters of HDL particles obtained with our gel system and the conventional Pharmacia PAA 4/30 gel, we examined LpA-I and LpA-I/A-II fractions isolated by immunoaffinity chromatography. As mentioned above, these lipoproteins fractions were kindly provided by Dr. Marian Cheung (Northwest Lipid Research Laboratory, University of Seattle, Seattle, Wash.) and the corresponding diameters were determined using the 3–31% gels (SFBR 3/31, Alamo Gels, Inc., San Antonio, Tex.) following protein staining. FIG. 12A illustrates the lipid-stained bands obtained for whole plasma, LpB, LpA-I and LpA-I/A-II for one individual. In contrast to the protein-stained gels disclosed, for examples, in the paper "Altered particle size distribution of apoA-I-containing lipoproteins in subjects with coronary artery disease," Cheung et al., J. Lipid. Res. 32: 383–397 (1991) and the paper "High density lipoproteins and coronary atherosclerosis: A strong inverse relation with the largest particles is confined to normotriglyceridemic patients," Johansson et al., Arterioscl Thromb 11: 177–182 (1991), only one or two major bands could be visualized with the lipid stain. For most samples, two lipid-rich bands can always be identified for LpA-I and only one for LpA-I/A-II. Only the major bands with the greatest area under the peak based on the protein stain were selected in this comparison. The two estimates of HDL particle diameters for LpA-I and LpA-I/A-II from 11 individuals were highly correlated (r=0.978 for a total of 37 peaks). We used this linear regression equation to calculate the adjusted particle diameters of the $HDL_2$ and $HDL_3$ in our calibrator. A new gel constant was derived using these adjusted diameters and FIG. 12B illustrated the correlation between the particle diameters for HDL subfractions determined on the S-GGE 2.8/8.30 using the gel constant approach and the values obtained by Dr. Cheung using the SFBR 3/31 gel and the Rf approach. The slope of the linear regression was 0.948 with an intercept of 0.4 nm (r=0.97).

Effect of Sample Storage on LDL and Lp(a) Particle Diameter

Figure 13:
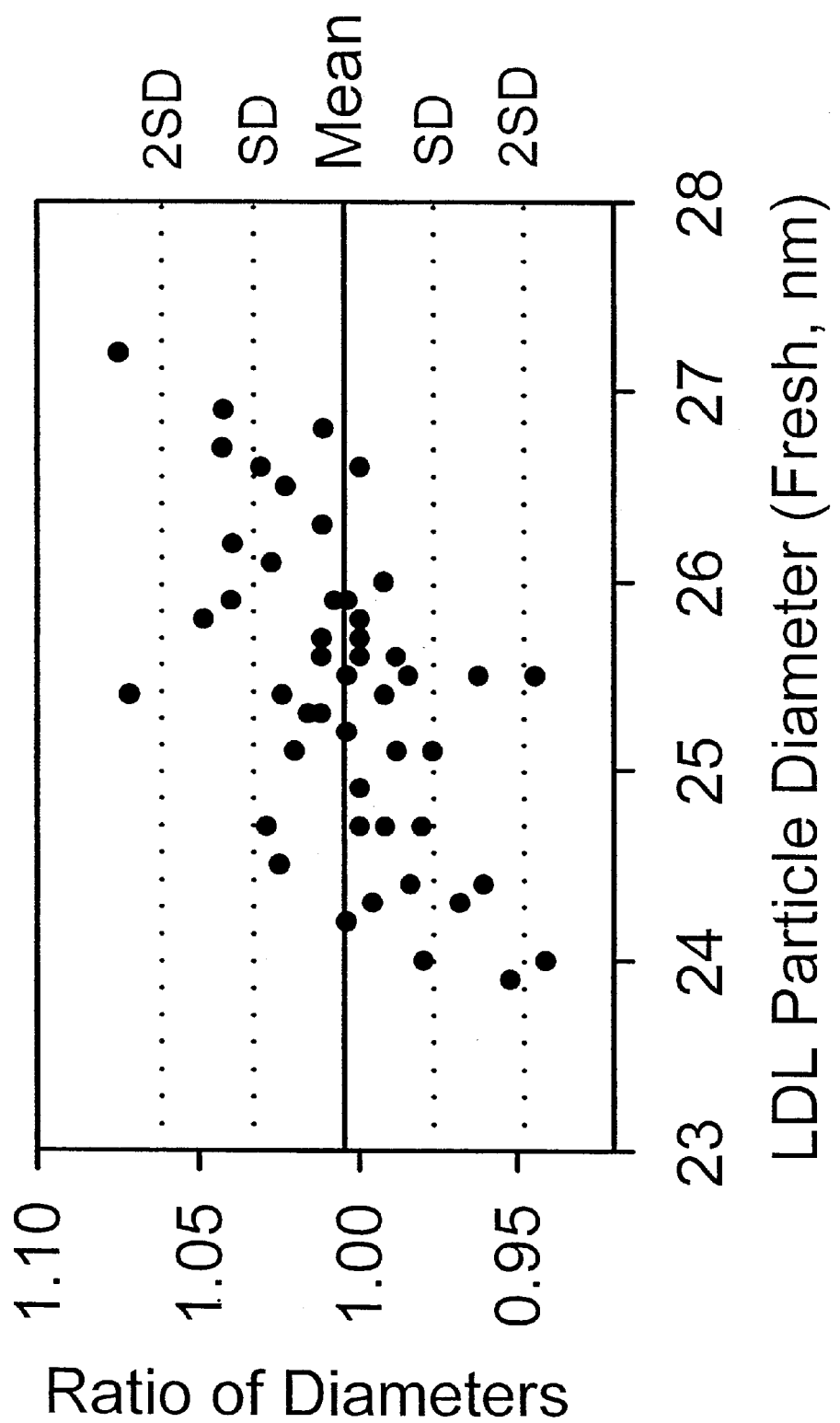
FIG. 13 shows the effect of sample storage on LDL particle diameter, where plasma samples from 51 subjects including normolipideric controls and patients with various forms of dyslipidemia were electrophoresed fresh (within 7 hrs of sample collection) and after storage at −80° C. (3 to 12 months in cryovials without any additives): no statistically significant difference was found between the two estimates by two-tailed paired t-test. The ratio of the two estimates of LDL particle diameters (Fresh/Frozen) is plotted as a function of LDL particle diameter determined from freshly isolated plasma. The mean ratio (-), 1 SD (---) and 2 SD lines (--) are also plotted. The variability in the ratio reflects the combined effect of sample storage and gel reproducibility.

FIG. 13 illustrates the reproducibility of lipoprotein particle size between fresh samples and frozen samples from a group of 52 individuals including normolipidemic controls and subjects with varying degrees of hyperlipidemia. Fresh plasma samples were analyzed as they were available (within 7 hrs of collection) using as many as 20 separate gels. Frozen samples were analyzed at the end of an 8-month storage period using four separate gels within a 2-week period. The mean (±SD) LDL particle diameter for the group was 25.7 nm (±0.807) based on the analysis of freshly isolated plasma and 25.3 nm (±0.693) when analyzed from frozen plasma samples. There was no statistically significant difference between the two measurements by two-tailed paired t-test. The mean (±SD) ratio of LDL diameter between the fresh and the frozen estimate was 1.0077 (±0.028). In 26.9% (17 of 51) of the samples, the ratio of the two estimates of LDL particle diameters (fresh vs. frozen) was greater than 3.27% (outside 1 SD) following a single freeze-thaw cycle. For 7.7% of the plasma samples (7 of 52), the ratio of the size estimates for LDL was greater than 6% (outside 2 SD) following a single freeze-thaw cycle. One third of the samples (16 of 52) were actually stored for 12 months prior to re-analysis. Since there were no differences in the estimates for particle diameter with longer storage, results from these samples were included in the final analysis.

In the present report we have described a protocol for the preparation of a gradient gel system consisting of two linear gradients, an 8–30% gradient for particles in the range of HDL and a 2–8% gradient for LDL and larger lipoprotein particles. The present system offers several advantages over existing systems previously described in the literature. Using commonly available gel casting equipment and conventional electrophoretic supplies, this protocol allows the reproducible preparation of gradient gels which can accommodate up to 21 samples per gel, or 42 samples per run with a dual-gel electrophoretic chamber. The protocol allows the application of pre-stained plasma samples and the gel can be scanned for particle size immediately at the end of the electrophoretic procedure. Elimination of the extensive staining and de-staining steps after electrophoresis should also minimize the need to handle the gel preventing any artifact that these steps may introduce. More importantly, the use of a lipid stain allows the specific visualization of only the lipoprotein fractions present in whole plasma.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

For example, a computer can be used to coordinate the motion of the movable arm and the rate of flow according to the width of the gel to yield better gradient gels.

What is claimed is:

1. A method for making a gel comprising the steps of:
   a. holding a solution in a reservoir;
   b. transferring the solution to a dispensing tip;
   c. delivering the solution to a gel chamber with a longitudinal axis by moving the dispensing tip along the longitudinal axis in a continuous motion; and
   d. curing the delivered solution in the gel chamber to form the gel.

2. A method for making a gel, comprising the steps of:
   a. holding a plurality of solutions in a plurality of reservoirs;
   b. forming a fluid of at least one solution from the plurality of solutions;
   c. transferring the fluid to a dispensing tip;
   d. delivering the fluid to a gel chamber with a longitudinal axis by moving the dispensing tip along the longitudinal axis in a continuous motion; and
   e. curing the delivered fluid in the gel chamber to form the gel.

3. The method of claim 2, wherein each solution of the plurality of solutions is a polyacrylamide solution with a unique concentration.

4. A method for making a gradient gel, comprising the steps of:
   a. holding a first solution at a first reservoir and a second solution at a second reservoir;
   b. connecting the first reservoir and the second reservoir with a channel;
   c. connecting an outlet with the second reservoir, wherein the outlet communicates with the channel so that a fluid of the first solution and the second solution is formed at the outlet;
   d. transferring the fluid to a dispensing tip;
   e. delivering the fluid to a gel chamber with a longitudinal axis by moving the dispensing tip along the longitudinal axis in a continuous motion; and
   f. curing the delivered fluid in the gel chamber to form the gradient gel.

5. The method of claim 4, wherein the first solution is a polyacrylamide solution with a first concentration.

6. The method of claim 5, wherein the second concentration is no less than the first concentration.

7. The method of claim 4, wherein the second solution is a polyacrylamide solution with a second concentration.

8. The method of claim 7, wherein the second concentration is no less than the first concentration.

9. A segmental linear gel made according to the method of claim 4.

10. A method for making a plurality of gels, comprising the steps of:
    a. holding a plurality of solutions in a plurality of reservoirs;
    b. forming a plurality of fluids, each fluid having at least one solution from the plurality of solutions;
    c. transferring the plurality of the fluids to a plurality of dispensing tips, each dispensing tip having one fluid therein;
    d. delivering the plurality of the fluids to a plurality of gel chambers positioned in parallel thereby defining a longitudinal axis by moving the dispensing tips along the longitudinal axis, so that each of the plurality of the dispensing tips delivers one fluid therein in motion into one of the gel chambers; and
    e. curing the delivered fluids in the plurality of the gel chambers to form the plurality of the gels.

11. The method of claim 10, wherein each solution of the plurality of solutions is a polyacrylamide solution with a unique concentration.

12. A segmental linear gel, comprising:
    a. a first segment comprising a linear polyacrylamide gradient of high to medium polyacrylamide concentration; and
    b) a second segment comprising a linear polyacrylamide gradient of medium to low polyacrylamide concentration, wherein the second segment is on top of and in continuous communication with the first segment.

* * * * *